United States Patent [19]

Playfair et al.

[11] Patent Number: 5,726,166
[45] Date of Patent: Mar. 10, 1998

[54] MALARIA TREATMENTS

[75] Inventors: John Hugh Lyon Playfair; Janice Taverne, both of London; Clive Alan Winston Bate, Oxford, all of United Kingdom

[73] Assignee: British Technology Group Limited, London, United Kingdom

[21] Appl. No.: 290,706

[22] PCT Filed: Jan. 15, 1993

[86] PCT No.: PCT/GB93/00084

§ 371 Date: Dec. 5, 1994

§ 102(e) Date: Dec. 5, 1994

[87] PCT Pub. No.: WO93/15761

PCT Pub. Date: Aug. 19, 1993

[30] Foreign Application Priority Data

Feb. 13, 1992 [GB] United Kingdom ............ 9203039

[51] Int. Cl.$^6$ .................. A61K 31/66; A61K 35/12; A61K 31/04

[52] U.S. Cl. ............... 514/129; 514/738; 424/520

[58] Field of Search .................. 424/520; 514/129, 514/738

[56] References Cited

PUBLICATIONS

Mintzer et al, 1988, Antimicrobial Agents and Chemotherapy vol. 32(3) pp. 391–394.

*Primary Examiner*—Russell Travers
*Attorney, Agent, or Firm*—Nixon & Vanderhye P.C.

[57] ABSTRACT

A method of treating or preventing clinical manifestations associated with diseases caused by infectious organisms which express antigens which in the patient stimulate secretion of harmful levels of at least one cytokine, other than diseases caused by organisms which stimulate secretion of cytokines only by expression of lipopolysaccharide, which method comprises administering to a human in need thereof an effective non-toxic amount of a material selected from the group consisting of inhibitors and immunogens wherein said inhibitors are pharmacologically acceptable materials which, in vitro, reduce or abolish secretion, by at least one of human monocytes and mouse peritoneal macrophages, of tumour necrosis factor following stimulation with a phospholipid-containing; tumour necrosis factor-inducing antigen other than lipopolysaccharide, and wherein said immunogens are pharmacologically acceptable materials comprising at least one B-cell epitope and which stimulate production of antibodies which, in vitro, reduce or abolish secretion, by at least one of human monocytes and mouse peritoneal macrophages, of tumour necrosis factor following stimulation with a phospholipid-containing, tumour necrosis factor-inducing antigen other than lipopolysaccharide. Examples of inhibitors include inositol monophosphate and phosphatidyl inositol lipids. Immunogens include these inhibitors optionally with carrier proteins.

6 Claims, 12 Drawing Sheets

Fig.4.

| INHIBITOR | |
|---|---|
| NONE | |
| INOSITOL MONOPHOSPHATE (20 μg per ml) | |
| PHOSPHATIDYL INOSITOL (20 μg per ml) | |

TNF TITRE (log 4)

Fig.5.

PERCENTAGE INHIBITION

RECIPROCAL DILUTION OF DETOXIFIED P.YOELII

μg/ml

MALARIA TREATMENTS

This application is a 371 of PCT/GB93/00084 filed Jan. 1, 1993.

The present invention relates to the treatment and prevention of malaria and certain other infectious diseases, especially to materials for use in such treatment and prevention.

Malaria is caused by organisms of the genus Plasmodium which infect and multiply within erythrocytes. Blood-stage infection is usually characterised by severe fever, sometimes accompanied by anaemia, hypoglycemia, pulmonary oedema, renal or hepatic failure, and coma which may occasionally prove fatal. Immunity may develop so as to reduce the severity of infection but takes many years and in individuals living in endemic areas complete elimination of parasites rarely occurs. Nevertheless, children from these areas do appear to develop resistance to the above clinical manifestations of infection even while carrying heavy parasite loads.

The conventional approaches to controlling malaria have aimed at:

(a) preventing the spread of the disease by eliminating the mosquito vector or (b) killing or controlling the parasite by chemotherapy. Insecticides have not been effective in controlling the mosquito due to the rapid development of resistance and also present environmental difficulties rendering this approach unsatisfactory. Chemotherapy has been relatively effective but is expensive; there are dangers to the patient if the parasites are killed too rapidly and supportive measures are generally required to deal with the major effects of the disease, such as hypoglycaemia which is treated by administration of glucose. Experimental vaccines aimed at eliminating one or other stages of the parasite are under trial but do not seem to protect all individuals. None of these control measures have been fully successful and the disease is on the increase world wide. Protection can be provided by various drugs for those travelling to endemic regions, but this is not a practical solution for the whole at-risk population.

Various investigators have observed that the major clinical problems raised by episodes of malarial disease are associated with the over-secretion of tumour necrosis factor (TNF), and possibly, other cytokines and that secretion of cytokines by macrophages can be stimulated in vitro by malaria antigens. This originally led the present inventors and their collaborators to postulate that antigens which stimulated cytokine release by macrophages would be particularly useful in generating anti-disease immunity against malaria [Playfair et al. Immunology Today, 1990, 11, 25], resulting in work on "antigen 7" published in, for instance, PCT/DK90/00159 (WO-A-90/15621). It has now been appreciated that these antigens could themselves induce many of the clinical problems associated with malaria and that they would be unlikely to be acceptable for use in humans. Others have proposed that secretion of TNF and other cytokines might be prevented by various agents acting directly to destroy or disable the macrophages, or have attempted to remove circulating cytokines from the bloodstream, for instance using anti-TNF antibodies. However both techniques have disadvantages in that they might compromise aspects of the patient's immune response to this and other diseases. Moreover a patient's macrophage population rapidly recovers from the action of direct-acting agents and this makes it unlikely to be practical to treat malaria in this manner.

On the basis of further investigations the present inventors believe that TNF and other cytokines are secreted by sensitive macrophages as a direct result of binding of malaria antigens to specific receptors on the macrophages; by interrupting this binding they consider that it is possible to treat or prevent the clinical manifestations of malaria. The strategy avoids the disadvantages of techniques used or proposed by others and would afford control of the disease while allowing the immune system of the patient to control the infection. It is not important that TNF should be the only or even the main cytokine induced by the disease organism, only that the organisms produce antigens which stimulate the relevant receptors on sensitive macrophages Following this theory, the inventors have identified certain features of the cytokine-stimulating antigens and the receptor enabling them (a) to produce inhibitors of the binding which may be used prophylactically or therapeutically against the disease and (b) to select immunogens which may be used to stimulate antibody production in at-risk and infected individuals so as to protect against the clinical manifestations of the disease. Furthermore, this insight has led the inventors to the view that certain other diseases, in which antigen binding to the same receptors, and corresponding release of cytokines, plays a leading role in causing the associated clinical manifestations, may be treated or prevented in similar manner. An example is sleeping sickness caused by African trypanosomes.

Gram negative bacteria also produce TNF-inducing antigens, known as lipopolysaccharide or LPS antigens, but it appears that these act at different receptors such that the inhibitors of the present invention do not significantly affect the course of these bacterial diseases. Similarly, agents intended to prevent LPS-induced TNF secretion have little effect on the receptors involved in oversecretion of cytokines induced by malarial antigens. The present invention is therefore concerned with treatment of diseases caused by infectious organisms which express antigens which stimulate harmful levels of TNF and/or other cytokines other than diseases caused by organisms which stimulate TNF and/or other cytokine secretion via LPS and the LPS receptor. Accordingly the following description will refer to the diseases to be treated as "non-LPS diseases" and to the cytokine-inducing antigens involved as "non-LPS antigens". The organisms involved are hereafter referred to as "non-LPS organisms" for consistency of terminology but it should be noted that certain non-LPS organisms which cause disease by the non-LPS mediated stimulation of cytokine oversecretion may also express LPS antigens.

The inventors have further observed that inhibitors of the antigen:receptor binding not only prevent the over-secretion of TNF and other cytokines but also have a rapid effect in countering the hypoglycaemia commonly associated with bouts of malaria. This effect on hypoglycaemia is not mediated by insulin and may therefore be achieved by a separate mechanism.

The present invention will be described below with reference to the figures of the accompanying drawings in which:

A BRIEF DESCRIPTION OF THE FIGURES

FIG. 1 shows: the inhibition of TNF induction by *P. yoelii* exoantigens by detoxified exoantigen Legend: Macrophages were incubated with serial dilution of detoxified preparation mixed with a single concentration of the active supernatant.

A. Exoantigen dephosphorylated by HF treatment.

A representative experiment showing inhibition of an active preparation that stimulated the production of 102,400

U per ml of TNF by incubation in the presence of a detoxified preparation.

B Exoantigen detoxified by lipase digestion. Means±SD obtained with 3 different active preparations incubated in the presence of one detoxified preparation.

FIG. 2 shows the effect of phosphatidyl inositol, inositol monophosphate and inositol on induction of TNF by P.yoelii exoantigens.

Legend: Preparations of P. yoelii exoantigens that induced the production of 18–36,000 U per ml of TNF were incubated with different concentrations of PI (o), IMF (●) and inositol (□); the results of typical experiments are illustrated. (The MW of the preparations of PI and IMP used are so similar that the figure would look no different if plotted in terms of molar concentrations).

FIG. 3 shows: titration of P.yoelii exoantigens in the presence and absence of inositol monophosphate.

Legend: Yields of TNF were determined from macrophages incubated with serial dilutions of an active supernatant made in medium (o) or medium containing 20 µg per ml of IMP (●).

FIG. 4 shows: the yields of TNF obtained from macrophages stimulated with LPS or P. yoelii exoantigens in the presence and absence of phosphatidyl inositol or inositol monophosphate. Legend: Black-bars=LPS (0.1 µg–1 µg per ml). Hatched bars=exoantigens. Results are means from 3 experiments with LPS and 14 with the exoantigens. FIG. 5 shows: the cross-inhibition of TNF induction by exoantigens of human parasites using detoxified P.yoelii exoantigens.

Legend: Inhibition of TNF production in response to exoantigens of P. falciparum (●) and P. vivax (o) by addition of serial dilutions of a lipase-digested P. yoelii supernatant. (Means±SD of 5 experiments for P. falciparum and 3 for P. vivax).

FIG. 6 shows the inhibitory effects of phosphatidyl inositol and inositol monophosphate on TNF induction by exoantigens of the human parasites.

Legend: Macrophages were incubated with a single concentration of the exoantigens and serial dilutions of the inhibitors. Means (±SD) of at least 3 experiments.

A: P. falciparum

B: P. vivax

Phosphatidyl inositol (o) Inositol monophosphate (●).

FIG. 7 shows the effect of pretreatment of macrophages on TNF induction by P.yoelii exoantigens.

Legend: Macrophages were pretreated for 30 mins with the reagents shown, washed, and then stimulated for 1 hr with different preparations of the exoantigens. They were then washed again, incubated overnight and TNF production assayed. PI and IMP were used at 20 µg per ml PE and PC at 50 µg per ml. The results with detoxified antigens represent 1 of 2 experiments; those with the phospholipids and IMP are means (±SD) of 6.

FIG. 8 shows the inhibitory effect of a PAF inhibitor on TNF induction by P.yoelii exoantigens and LPS.

Legend: Macrophages were incubated overnight with a 1/20 dilution of an exoantigen preparation or 0.2 µg per ml of LPS and different concentrations of the inhibitor. Pretreatment of the macrophages with 50 µg per ml of inhibitor was not toxic to the cells as the yields of TNF were unaffected. For legends to FIGS. 9 to 16, see Example 2. For legends to FIGS. 17 to 19, see Example 3.

FIG. 9

Inhibition of TNF induction by toxic antigens from P. falciparum and P. yoelii by antisera against IMP assayed using human PBMNC (●) and mouse peritoneal macrophages (o) respectively. Means (±SD) of 2 batches of antiserum, each tested twice against P. falciparum, and of 3 batches (including one of the above) tested against P. Voelii, two of them three times and one once.

FIG. 10

Inhibition of TNF induction by parasite antigens by antisera against PI-KLH.

A: Comparative titrations of antisera obtained after 1 (o) or 3 injections (●) of PI-KLH. Means (±SD) from 3 different batches of antiserum, each of which was titrated twice against P. yoelii and P. falciparum antigens.

B: Comparative titrations of affinity purified IgG and IgM from antiserum obtained after 3 injections of PI-KLH. Means of titrations of 2 preparations titrated against P. yoelii antigens that induced 38,956 U/ml of TNF from mouse macrophages. Original antiserum (o) IgG (●); IgM (■)

C: Titrations of antiserum obtained after 3 injections of PI-KLH before and after adsorption with various liposomes. Means of titrations of 2 serum samples titrated against P. yoelii antigens which stimulated the production of 56,000 U/ml of TNF from mouse macrophages. Liposomes used for adsorption: none (o); PC (●); PS; (■) PI (□);

FIG. 11

Inhibition of TNF induction by parasite antigens by antisera against PS-KLH.

A: Comparative titrations of antisera obtained after 1 (●) or 3 injections (o) of PS-KLH. Means (±SD) from 5 different batches of antiserum, titrated against P. yoelii or P. falciparum antigens.

B: Comparative titrations of affinity purified IgG and IgM from antiserum obtained after 3 injections of PS-KLH. Three different batches of serum were cooled before adsorption to isotype specific agarose; they were tested for their ability to inhibit TNF secretion from mouse macrophages stimulated with P. yoelii antigens.

Original antiserum (o); IgG (●); IgM (■)

C: Titrations of antiserum obtained after 3 injections of PS-KLH before and after adsorption with various liposomes. Means of titrations of 2 serum samples titrated against P. yoelii antigens which induced the production of 13,975 U/ml of TNF from mouse macrophages. Liposomes used for adsorption: none (o); PC (●) PS (■); PI (□).

FIG. 12

Prolongation of production of inhibitory antibody by immunisation with PI-KLH or PS-KLH. Pools of serum from groups of 3 mice bled at different intervals after 3 injections of PI-KLH, PS-KLH, unconjugated PI or P. falciparum antigens were titrated against P. falciparum antigens which induced the production of the order of 1,000 pg/ml of TNF from human PBMNC. PI-KLH (●); PS-KLH (o); PI (□); P. falciparum antigens (■).

FIG. 13

Inhibition of TNF induction by parasite antigens by antisera against phospho-threonine and galactosamine-1-phosphate conjugated to KLH. compared with antisera against PI-KLH and PS-KLH Mice were bled 12 days after 3 injections in each case and one group immunized with lysine conjugated to KLH is included as a control. Titrations were done against either P. falciparum or P. yoelii antigens and are the means of results obtained with antisera raised against 2 preparations each of phospho-threonine-KLH and galactosamine-1-phosphate-KLH, 3 of PI-KLH, 5 of PS-KLH and 3 of lysine-KLH. P-threonine-KLH (■); galactosamine-1-P-KLH (□); PI-KLH (●); PS-KLH (o); lysine-KLH (Δ)

FIG. 14

Titrations of antiserum against phospho-threonine-KLH and galactosamine-1-phosphate-KLH before and after adsorption with various liposomes.

A: Phospho-threonine-KLH; B: Galactosamine-1-phosphate-KLH. Means of 2 different antisera in each case, titrated for their ability to inhibit the induction of TNF by mouse peritoneal cells stimulated with *P. yoelii* antigens. Liposomes used for adsorption: none (●); PC (o); PI (□), PS (■).

FIG. 15

The effect of antiserum against KLH conjugates on the induction of TNF secretion by other stimulants. Various stimulants were incubated in the presence or absence of antiserum against PI-KLH (black bars) or against PS-KLH (hatched bars) diluted 1/1500 and the amount of TNF secreted by PBMNC was determined. The results are means (±SD) of at least 4 tests, expressed as a percentage of the control without antibody.

FIG. 16

Induction of hypoglycaemia by parasite toxic antigens injected into mice immunized with various KLH conjugates. Means (±SD) of blood glucose of groups of 3 mice (6 for PS/KLH) injected i.p. with 0.5 ml of a preparation of *P. yoelii* antigens 12 days after 3 injections of the immunogens. Unimmunized (■); lysine-KH (□); PI-KLH (o); PS-KLH (●); P-Thr-KLH (Δ). Although the numbers in each group are small, in total 12 mice injected with phosphorylated compounds gave significantly different results from the 6 controls at 4 and 8 hr (p=<0.0001 by Students T test). Similar results were obtained in other experiments using outbred mice immunized with PI conjugated to BSA, PS-BSA and Gal-1-P-BSA.

EXAMPLE 3

Protection of mice by immunization. FIGS. 17 to 19 show results of experiments done with the lethal *P. yoelii* which killed all the control mice.

FIG. 17 illustrates protection induced by an untreated parasite culture supernatant, compared with a potent immunizing lysate that give anti-parasitic protection as opposed to the anti-disease protection we are interested in. It was published in our paper in Immunology Today 1990, 11, 25. The figure was based on about 4 mice. It was shown to make the point that this kind of immunisation is different from that of an anti-parasitic vaccine, in that the mice that survive do so for a prolonged period with a very high parasitaemia.

FIG. 18 illustrates the prolonged survival obtained in experiments in which mice were immunised with parasite supernatants which had been first boiled, then protease-treated and then deaminated (with nitrous acid). All these preparations were still active in vitro in terms of their ability to stimulate macrophages to secrete TNF. The mice were immunized with 0.5 ml of supernatant i.p. and infected 10 days later. We have pooled the results of several experiments so that the figure represents at least 20 mice per group. It is rare for mice to die after day 18, although the odd one did.

FIG. 19 illustrates the prolonged survival obtained with mice immunised with inositol monophosate (200 µgi.p.) or 2 mg of preparations of various liposomes. Again, we have pooled results to put up the numbers per group and again only the odd mouse died after day 18.

Inhibitors

In one aspect, the invention relates to inhibitors of TNF secretion which may be used therapeutically or prophylactically to treat or prevent the clinical manifestations of malarial disease and other non-LPS diseases, to the production and use of such inhibitors and to pharmaceutical compositions of them.

An inhibitor of the present invention is defined as a pharmacologically acceptable material which, in vitro, reduces or abolishes TNF secretion by human monocytes or mouse peritoneal macrophages following stimulation with phospholipid-containing TNF-inducing non-LPS antigens.

The inhibitors of the invention are effective because they prevent or reduce the binding of the non-LPS antigen(s) produced by the pathogenic organism to the relevant receptor. This can be achieved in one of two ways: either the inhibitor binds to the receptor or it binds to the antigen. In each case it is necessary for the inhibitor to bind in such a way that it will hinder binding between the relevant portions of the receptor and the antigen and the simplest way to achieve this is to use materials which mimic structural features of the antigen or receptor binding sites.

One particular class of inhibitors of the invention comprises materials which mimic a portion of the antigen and can therefore bind to the receptor but which lack all the structures of the antigen required to induce TNF or cytokine secretion. Known compounds which fulfil these criteria are inositol monophosphate (IMP) and certain phosphatidyl inositol (PI) lipids. PI lipids may bear one or two fatty acid side chains such as palmitoyl, stearyl and lauryl groups. Other compounds which may be used in this manner include phosphatidyl serine (PS) and phosphatidyl threonine (PThr) lipids and phosphorylated sugars such as mannose, glucose, galactose and fructose but not glucosamine. Other materials which are candidates for use as such inhibitors include degradation products of non-LPS TNF-inducing malaria antigens or other parasite non-LPS exoantigens whose TNF-inducing activity has been abolished. The exoantigens in question may be related to membrane-bound antigens having a glycosyl phosphatidyl inositol (GPI) anchor or similar structure which fulfils the same membrane-binding function.

GPI anchors are found on many protein or polysaccharide antigens (whether or not associated with malaria and other protozoal parasite diseases) and comprise a carbohydrate moiety linking the antigen to a glucosamine group which is, in turn, bound to one of the inositol carbons of a PI lipid molecule.

Any protozoal non-LPS antigen which in vitro induces TNF-secretion by human monocytes or mouse peritoneal macrophages and whose TNF-inducing activity can be reduced by chemical or enzymatic treatment is a potential source of inhibitors according to the present invention. Before use as an inhibitor the antigen must be treated so as to reduce or abolish the TNF-inducing activity which may be achieved, for example, by suitable degradation reactions. Degradation techniques which may be employed include lipase digestion, deacylation, dephosphorylation and phospholipase C digestion such as described in Example 1.

The strain or species of parasite from which the exoantigen is derived is not particularly important and it is therefore conceivable that, for example, malarial antigen degradation products and trypanosomal antigen degradation products could each be used to treat both malaria and sleeping sickness.

Another class of inhibitors of the invention comprises materials which mimic a portion of the binding site on the receptor and which can therefore bind to the antigen. Such materials would include synthetic, semisynthetic or recombinant receptor molecules or fragments thereof bearing the binding site or receptor molecules or fragments thereof obtained by extraction and purification from suitable monocytes or peritoneal macrophages. Techniques for producing such materials are within the ability and knowledge of those skilled in the art.

A further class of inhibitors of the invention comprises antibodies and fragments thereof, such as F(ab')$_2$ and Fab fragments, single domain antibodies and recombinant antibody-like polypeptides. These antibodies and fragments thereof bear a suitable antigen-binding site which is capable of binding to the relevant receptor molecule on monocytes and peritoneal macrophages or to the TNF-inducing antigen of the non-LPS pathogen in such a way as to prevent or reduce binding between the TNF-inducing antigen and the receptor. It should be noted that such antibodies and fragments need not be directed against the actual binding site of the TNF-inducing antigen or its receptor; provided that the antibody or fragment is sufficiently bulky and binds to the antigen or receptor sufficiently close to the binding site thereof, steric effects will diminish the binding of the antigen to the receptor. Techniques for producing such antibodies and fragments are within the ability and knowledge of those skilled in the art.

Yet another class of inhibitors according to the present invention comprises the serum components known to bind to phospholipids such as β2-glycoprotein-1 (also known as apoprotein-H) and low and high density lipoproteins (LDL and HDL) and C-reactive protein.

The inhibitors and antibodies or fragments thereof according to the invention may be used in conventional manner as prophylactic or therapeutic agents. Administration of antibodies or fragments thereof may be regarded as passive immunisation. Active immunisation is described below in relation to immunogens of the invention.

The present invention therefore provides the use of an inhibitor as hereinbefore defined in the preparation of a medicament for use in the treatment or prevention of clinical manifestations associated with infection by a TNF-inducing non-LPS organism.

The invention further provides a method of treatment of an individual infected with or at risk of infection with a non-LPS organism by administering a non-toxic amount of an inhibitor as hereinbefore defined sufficient to treat or prevent clinical manifestations associated with said infection.

The invention further provides an inhibitor as hereinbefore defined other than IMP and PI lipids for use in a method of treatment of the human or animal body by therapy, especially to treat or prevent clinical manifestations associated with infection with a non-LPS organism.

The invention further provides an inhibitor as hereinbefore defined which is a degradation product of a TNF-inducing non-LPS antigen-of a non-LPS organism.

In each of the above it is preferred that the non-LPS organism is a protozoal parasite such as *Trypanosoma gambiense* or *T. rhodesiense* or a plasmodial parasite, more preferably a plasmodial parasite and most preferably *Plasmodium falciparum, P. vivax, P. malaria* or *P. ovale*.

Preferably the clinical manifestations which are treated or prevented include hypoglycaemia and/or anaemia and/or fever. Preferred inhibitors according to the present invention comprise the delipidated, deacylated, dephosphorylated or otherwise deactivated degradation products of phospholipid dependent TNF inducing malarial antigens, IMP and dipalmitoyl, dilauryl and distearyl phosphatidyl inositol.

The inhibitors of the present invention may be used as the pure compound but are preferably administered in the form of a pharmaceutical composition.

The present invention therefore provides a pharmaceutical composition for treating or preventing the clinical manifestations of infection by a non-LPS organism comprising an inhibitor as hereinbefore defined and a pharmaceutically acceptable carrier or diluent therefor.

Suitable carriers and diluents will depend upon the chosen route of administration and other criteria well known to pharmacists. For administration as tablets and powders the diluent or carrier may be any suitable inert binding or filling agent. For administration as liquids the diluent or carrier will be a liquid such as water for injection, demineralised water or a non-aqueous liquid such as an oil. The compositions may also contain accessory ingredients such as antioxidants, antimicrobial agents, buffers and, especially for injectable compositions, agents to adjust the tonicity of the composition.

The compositions may be administered by any suitable route such as orally or parenterally for instance by intravenous, intranasal, intramuscular or subcutaneous injection or infusion. As the objective will often be to provide whole-body treatment and prevention of clinical manifestations and as the presence of substantial quantities of the inhibitor may be required to maintain protection from the disease, administration by continuous infusion may be required or the use of depots and sustained release formulations should be considered.

The dosage administered should be sufficient to maintain protection from non-LPS antigens without deleterious side effects and can be ascertained by typical dose ranging experiments. The dosage will of course depend also on the size, weight, age and state of health of the recipient and the clearance rate of the inhibitor, the way the inhibitor is distributed around the body and its relative affinity and avidity for the macrophage receptor compared with that of the non-LPS antigens whose effect is to be countered. However it is presently contemplated that for IMP doses in the region of 1 to 100 mg/kg, would be administered at intervals of from a few hours to twice or even once daily and that the average daily dose for a normal adult would be in the range of from 1 to 1000 mg; for instance at least 10 mg.

Treatment using the inhibitors according to the present invention may be combined with other therapeutic or prophylactic measures. For instance, the inhibitors of the invention may be used to prevent adverse effects arising from destruction of the parasites using anti-parasitic agents. Alternatively, the inhibitors may be used in controlling the worst effects of an acute episode of a parasite infection in combination with other support measures such as treatment for hypoglycaemia and anaemia.

Immunogens

Whereas the inhibitors of the invention are used prophylactically or therapeutically to interrupt the binding of non-LPS antigens to the relevant receptor, immunogens are used to generate active immunity in individuals at risk. Immunogens of the invention are also useful in generating antibodies in host animals and thus for providing polyclonal, monoclonal or recombinant antibodies and fragments thereof for use as inhibitors of the invention.

The immunogens of the invention will be pharmacologically acceptable materials capable of stimulating production of antibodies which antibodies reduce or abolish production of antibodies which antibodies reduce or abolish the in vitro secretion of TNF or other cytokine by human monocytes or mouse peritoneal macrophages following stimulation with phospholipid-containing TNF-inducing non-LPS antigens.

The immunogens of the present invention will contain a suitable B-cell epitope. This enables the stimulation of circulating antibodies in an individual at risk or a host animal and will be sufficient to provide short term protection for instance for individuals travelling to areas where non-LPS organisms are endemic, and will be sufficient to generate antibodies and antibody-secreting cells in host animals which may be used as, or in the production of inhibitors as discussed above.

The immunogens of the invention may also contain an appropriate T-cell epitope in which case they will stimulate memory cells in immunised individuals thereby providing long term protection against repeated exposure to the non-LPS organisms.

Inhibitors as described above may be used as immunogens of the invention provided that they are sufficiently large molecules to be immunogenic in their own right. Inhibitors which are not sufficiently large may be bound to carrier proteins in conventional manner for use as immunogens. Fragments of the TNF-inducing antigens which do not contain the receptor-binding site as such and fragments of the receptor molecule which do not contain the antigen-binding site as such may be used as immunogens provided that they stimulates production of antibodies which will block the antigen: receptor binding. The TNF-inducing antigens, or fragments thereof containing the receptor binding site may be used as immunogens in accordance with the invention in host animals and may also be used to treat humans; where appropriate, at least in the latter case, the TNF-inducing activity will be reduced or abolished, for instance by degradation as described above. Receptor molecules and fragments thereof containing the antigen-binding site may also be used as immunogens of the invention in host animals and may also be used to treat humans provided, in the latter case at least, that any suitable precautions are taken to avoid stimulating undesirable auto-immunity to the intact receptor molecules on the patient's cells.

Preferred immunogens of the present invention are PI, PS or PThr lipids, IMP, phosphorylated sugars such as glucose, galactose, fructose and mannose but not glucosamine and degraded TNF-inducing antigens as described above and such materials bound to a carrier protein, preferably tetanus toxoid or keyhole limpet haemocyanin or more preferably an exoantigen of a non-LPS protozoal parasite.

Phospholipid liposomes and phosphorylated sugars, especially monosaccharides may also be used as immunogens according to the invention is they can generate antibodies against phosphate groups which can bind the non-LPS antigens. It is not important which phospholipids or sugars are used though PI and phosphatidyl serine phospholipid liposomes are preferred.

The immunogens of the invention will be used in conventional manner, preferably in combination with suitable adjuvants such as aluminium hydroxide gel for humans or Freunds complete or incomplete adjuvant or saponin for host animals, as ISCOMS or in liposomes. They may be administered by any conventional route such as intradermally or subcutaneously, intramuscularly or intravenously and, for animals, intraperitoneally, in the form of suitable pharmaceutical formulations. Preferably the immunogens are presented as solutions or suspensions in water for injection or as dry powders for reconstitution with pyrogen-free water or water for injection, and may also contain suitable buffers, antioxidants, preservatives and agents for adjusting the tonicity.

Suitable dosage regimes depend on the desired immune response but typically involve at least one and possibly several repeat injections at intervals of a few days, such as one or two weeks, up to a few months, such as 1, 2, 3 or 6 months and possibly with boosters at intervals of one or more years for instance up to 5 years.

Suitable dosages will depend upon the immunogenicity of the material administered but will typically be in the range of 1 to 1000 mg for an adult human.

The invention will be further illustrated by the following Example which is not intended to limit the scope of the invention in any way:

EXAMPLE 1

It has previously been shown that malaria parasites liberate exoantigens which, through a phospholipid component, stimulate mouse macrophages to secrete tumour necrosis factor (TNF) and are toxic to D-galactosamine-sensitised mice, and which therefore might be involved in pathology. *Plasmodium yoelii* expamtoges detoxified by dephosphorylation or digestion with lipases do not induce TNF production. However, these partial structures inhibited its production in response to the exoantigens, though not to bacterial lipopolysaccharide (LPS).

When pure phospholipids were tested in a macrophage assay, none stimulated the production of TNF but phosphatidyl inositol (PI) inhibited TNF induction by *P. yoelii* exoantigens. Moreover, inositol monophosphate (IMP) was the only one of a number of monophosphate saccharides tested which was inhibitory:inositol was not. Macrophages pretreated with PI, IMP or detoxified exoantigens and then incubated with parasite exoantigens also yielded much less TNF. PI, IMP and lipase-digested. exoantigens of *P. yoelii* inhibited the TNF-inducing activity of exoantigens of the human parasites *P. falciparum* and *P. vivax* similarly. Neither PI nor IMP diminished TNF production in response to LPS, in contrast to a platelet-activating factor antagonist (1-O-hexadecyl-2-acetyl-sn-glycero-3-phospho(N,N,N-trimethyl)hexanolamine) which inhibited both exoantigen and LPS-induced production of TNF.

It is concluded that at least two different parts of the molecule are involved in the induction of TNF secretion by parasite exoantigens: one requires the presence of a phosphate bound to inositol and, since dephosphorylated exoantigens were also inhibitory, one does not. It would seem that both affect interactions between parasite-derived exoantigens and the machrophage receptors.

INTRODUCTION

Cytokines such as tumour necrosis factor (TNF) and interleukin-1 (IL-1) have been shown to induce fever (15), and the results of a recent clinical trial of a monoclonal antibody against TNF suggest that the fever of malaria is indeed mediated by TNF(29). Furthermore, several studies have shown that there is a significant association between circulating levels of TNF and the complications of *Plasmodium falciparum* infection (19,24,28). The involvement of TNF in the illness and pathology of malaria has been well reviewed by Clark and his co-workers(14).

It has already been shown that human and rodent malaria parasites release exoantigens, which stimulate macrophages to secrete TNF in vitro (7,41) and are toxic to mice pretreated with D-galactosamine to sensitise them to TNF (8). It would seem that the antigens are released at schizont rupture (27) and this could explain the well-known association between fever and this stage of the parasite's developmental cycle. The exoantigens are highly immunogenic, giving rise to antibody which blocks their ability to induce TNF in vitro and protects D-galactosamine-sensitised mice from their toxic effects (5). We have proposed that the presence of such antibody might account for the "antitoxic" immunity that is acquired by people living in areas where malaria is endemic and have suggested that the exoantigens might be candidates for an antidisease vaccine (34).

Some years ago Clark pointed out (13) that many of the symptoms of malaria have features in common with those of endotoxaemia, and it is now recognised that the latter is associated with TNF induced in the host by lipopolysaccharide (LPS) released from the bacteria responsible for Gram-negative sepsis (11). Indeed, monoclonal antibodies against TNF (43) and against lipid A, the part of the LPS molecule that mediates many of the biological activities of LPS including its toxicity, can protect animals against lethal bacteriaemia (35). In order to characterise the molecular structures of LPS that lead to the induction of septic shock, the activity of various partial structures of LPS have been studied. Lipid X, for example, is a non-toxic intermediate in the biosynthesis of lipid A whose structure resembles half that of the lipid A molecule. Purified lipid X does not induce the production of TNF (2, 26, 30, 31) but inhibits various biological activities of LPS in vitro and its toxicity for mice (30, 36). Lipid $IV_A$, another partial structure, similarly failed to induce the production of TNF, but also inhibited its induction by LPS; these results have been explained by competition for LPS receptors on target cells (26).

Although the phospholipid-containing malaria exoantigens are clearly different from LPS (40) and apparently stimulate macrophages through different receptors (41), there are some functional analogies. In the present Example, various "detoxified" preparations of parasite exoantigens (that is, those which were not toxic to mice and did not induce TNF production by macrophages) are tested to see if they could inhibit its induction by active preparations of parasite exoantigens. We also examined the ability of some molecularly defined phospholipids and of some monophosphate saccharides both to induce the production of TNF and to inhibit the TNF-inducing activity of the exoantigens. The results obtained with exoantigens derived from the rodent parasite *P. yoelii* were confirmed with samples from the human parasites *P. falciparum* and *P. vivax*. The TNF-inducing component of the exoantigens appears to be phospholipid, in that its activity is destroyed not only by digestion with lipases but more specifically by digestion with phospholipase C; it is also inactivated by dephosphorylation by hydrofluoric acid. To investigate the specificity of this inhibition, we compared the effects of the various compounds found to inhibit the induction of TNF by the exoantigens for their effects on induction by LPS. Finally, we examined the ability of an antagonist of platelet-activating factor (PAF) to inhibit induction by both LPS and the exoantigens. PAF, itself a phospholipid, is an endogenous mediator that causes shock (21) and is released in endotoxaemia (12) and it has been shown that a PAF antagonist can block necrosis induced by LPS through the release of TNF (38).

Materials and Methods

Mice. Outbred females at least 6 weeks old were used (Tuck No1; A. Tuck & Sons, Battlesbridge, Essex).

Rodent parasites. The YM lethal variant of *P. yoelii* (obtained from D. Walliker, Edinburgh University) was used (18). Mice were injected intravenously with $10^1$ parasitized erythrocytes, and parasitaemia was determined from blood films stained with Giemsa.

Preparation of exoantigens. Since TNF-inducing activity was not associated with protein but was enhanced by its removal, all exoantigen preparations were incubated for 24 h at 37° C. in 10 µg per ml of pronase E (Sigma), boiled and dialysed against PBS. No protein was then detectable by BioRad assay (<1 µg per ml). Before use, they were mixed with polymyxin B-agarose (Sigma) to remove any endotoxin, centrifuged at 500×g for 10 min and sterilised by filtration through a 0.2 µm-pore-size membrane filter (Flow Laboratories, Irvine, Ayrshire, United Kingdom) and stored a 4° C.

Exoantigens of *P. yoelii*. As described previously (39), exoantigens were prepared from mice with high parasitaemia bled by cardiac puncture. The erythrocytes were washed twice in sterile phosphate-buffered saline (PBS) and then suspended in PBS at $10^k$ parasitized cells per ml in suspension on a roller at 37° C. for 24 h. Next day the suspensions were centrifuged at 500×g for 10 min. The supernatant was then boiled for 5 min and centrifuged at 1,300×g for 10 min; these supernatants were then passed through a membrane filter and stored at 4° C. Detoxification of *P. yoelii* exoantigens. (1) By treatment with lipase: Exoantigen preparations in PBS were incubated overnight at 37° C. with 2–5 U per ml of wheat germ lipase bound to agarose (Sigma) which was the removed by centrifugation at 500×g for 10 min. The supernatants were sterilised by filtration and stored at 40° C.

(2) By dephosphorylation: Lyophilised samples were dissolved in 46% HF and kept at 0° C. in polythene tubes for 22 h; they were then diluted with PBS and neutralised with NaOH. Precipitates were removed by centrifugation at 1,300×g for 10 min and the supernatants were sterilised by filtration and stored at 4° C.

Exoantigens of *P. falciparum*: These were kindly provided by Dr D. Kwiatkowski of Oxford University. They had been prepared by incubating schizont-enriched preparations from a continuous culture system in minimum essential medium without serum at 37° C. for 24 h. The cultures were then centrifuged and the supernatants collected and boiled for 5 min. The preparations were centrifuged again and the supernatants obtained were passed through a membrane filter and stored at 4° C.

Exoantigens of *P. vivax:* These were kindly provided by Prof. K. Mendis, University of Colombo. Erythrocytes obtained from 3 patients infected with *P. vivax* at a time when the parasites had become schizonts were washed and concentrated to about 80% parasitaemia. They were suspended in PBS without serum at 1×10/ infected erythrocytes/ml and incubated at 37° C. for 24 h on rollers. Supernatants were collected, passed through a 0.2 µm Millipore filter, boiled for 5 min, centrifuged again and the supernatants obtained were pooled and stored at 4° C.

Stimulation assays using mouse peritoneal cells. As described previously (5), cells were collected from mice given thioglycolate intraperitoneally 3–5 days previously, using Hanks balanced salt solution (Flow Laboratories) containing 1 U of heparin and 5 mg of polymyxin B (Sigma) per ml. Washed cells were suspended in 5% fetal calf serum in RPMI 1640 (Flow Laboratories) containing polymyxin B and adjusted to $10^7$ viable cells per ml; 0.1 ml volumes were then dispensed into wells of 96-well microtitre plates (Nunc, Roskilde, Denmark). The cells were incubated for 2 to 3 h at 37° C. to allow macrophages to adhere and then for 30 min with an equal volume of medium containing 2 µg of indomethacin (Sigma) per ml. Non-adherent cells were removed, the medium was replaced by 0.2 ml volumes of RPMI 1640 containing polymyxin B and the stimulants to be tested, and the cultures were incubated overnight. (Serial dilutions of the stimulants were always tested to establish a dose-dependent relationship, and experiments were repeated at least twice). The next day, supernatants were collected and assayed for TNF by their cytotoxicity for L929 cells. A 1/10 dilution of each was made in medium containing 5% fetal calf serum and 1 µg of emetine (Sigma) per ml and stored at −20° C. in case a titration needed to be repeated. Cultures incubated with serial dilutions of LPS or with medium alone were included in every experiment as positive and negative controls on the capacity of the macrophages to yield TNF. Inhibition assays. The agents to be tested were titrated for their ability to block the induction of TNF by mixing equal volumes of serial dilutions with a single concentration of an exoantigen preparation or of LPS before addition to the acrophage cultures. As phospholipids are light-sensitive, the plates were covered with aluminium foil.

TNF assays. TNF was assayed colorimetrically by its cytotoxicity for L929 cells (obtained from the European Collection of Animal Cell Cultures, Porton Down, Salisbury, Wiltshire) seeded at 2.5×10/ cells per well the day before, as described previously (8). Serial dilutions of macrophage supernatants were tested in duplicate in 0.1 ml volumes per well of 96-well microtitre plates in RPMI 1640 containing 1 µg emetine per ml. One unit is defined as the amount causing 50% cell destruction.

Other Reagents. LPS (phenol extract of *Escherichia coli* (055:B5), all phospholipids (phosphatidyl inositol from bovine liver (PI), phosphatidyl choline from egg yolk (PC), phosphatidyl serine from bovine brain (PS), phosphatidyl ethanolamine from bovine brain (PE), phosphatidic acid (PA) and cardiolipin from bovine heart (CL) and all the monophosphate saccharides tested were obtained from Sigma. A PAF antagonist, 1-O-hexadecyl-2-acetyl-sn-glycero-3-phospho-(N,N,N-trimethyl)hexanolamine, was obtained from Novabiochem.

Results

Inhibitory activity of detoxified exoantigens. The toxicity of parasite exoantigens and their ability to trigger macrophages to secrete TNF in vitro is mediated by a phospholipid, which accumulates in the chloroform/methanol phase of a two phase lipid extraction process (41), is destroyed by de-O-acylation by mild alkaline treatment and by treatment with lipases, and also by dephosphorylation and digestion by phospholipase C. We therefore looked to see whether exoantigens of *P. yoelii* that had been detoxified, either by dephosphorylation or by removal of fatty acids by lipase digestion, contained structures that could inhibit the ability of active preparations to stimulate macrophages to secrete TNF. Yields of TNF were compared with controls diluted in medium. Preparations that had been detoxified by either procedure caused a dose-dependent decrease in the amount of TNF produced. FIG. 1a shows the results of a typical experiment in which a dephosphorylated preparation was included with an active preparation which stimulate the production of 102,400 U per ml of TNF; FIG. 1b shows results (mean±SD) of experiments done with one lipase-digested preparation titrated against 3 different active preparations. Lipase-digested supernatants from uninfected mouse erythrocytes were not inhibitory. (As the results shown were obtained both with different detoxified exoantigen preparations and with stimulatory preparations, direct comparison of the inhibitory activity of preparations detoxified by the two methods cannot be made).

TABLE 1

TNF induction by *P. Yoelii* exoantigens and LPS: Specificity of inhibition.

| Inhibitor | Stimulus | Control[a] TNF titre (log 4) | Percent inhibition (Mean ± SD) |
|---|---|---|---|
| Lipase-digested exoantigen | Exoantigen | 4.9[b] | 99.7 ± 0.6 |
|  | LPS | 4.2[c] | 0 |
| Dephosphorylated exoantigen | Exoantigen | 4.4[d] | 99.6 ± 0.01 |
|  | LPS | 4.7[e] | 5.2 ± 7.1 |
| Lipase-digested LPS |  |  |  |
| 10 µg/ml | Exoantigen | 5.5 | 0 |
| 1 µg/ml | Exoantigen | 1.8 | 0 |
| 1 µg/ml | LPS | 3.0 | 100 |
| 1 µg/ml | LPS | 2.7 | 93.2 |
| 0.25 µg/ml | LPS | 2.7 | 87.4 |
| 0.06 µg.ml | LPS | 2.7 | 42.2 |
| 0.015 µg/ml | LPS | 2.7 | 24 |

LPS as a stimulus was used at 0.1 µg per ml throughout
[a]in the absence of inhibitor
[b]mean of 13 experiments
[c]mean of 2 experiments
[d]mean of 8 experiments
[e]mean of 4 experiments This inhibition of TNF induction was specific to the parasite exoantigens. These usually induce amounts of TNF of the same order as those obtained with ca. 1 µg per ml of LPS (41) but none of the exoantigen preparations detoxified by either means inhibited the induction of TNF by 0.1 µg per ml of LPS (Table 1).

Conversely, detoxified preparations of LPS which inhibited the induction of TNF by LPS did not affect induction by *P. yoelii* exoantigens. For example, digestion of 10 µg per ml of LPS by lipase totally abolished its activity and although 1 µg per ml of such detoxified preparations inhibited the induction of TNF by untreated LPS, 10 µg per ml did not affect the amount of TNF produced in response to the parasite exoantigens and 1 µg per ml did not decrease the activity of a diluted sample.

Inhibition by Phospholipids. As these results indicated that the activity of the *P. yoelii* phospholipid component could be inhibited competitively by the inactivated structure, we tested a number of different commercially available phospholipids to see if they too were inhibitory. PI consistently inhibited the TNF-inducing activity of the exoantigens; PC, PS, PE, PA and CL, at the same doses, did not (Table 2).

TABLE 2

Titres of TNF induced by *P. yoelii* exoantigens in the presence of various exogenous phospholipids.

| | | µg per ml | |
|---|---|---|---|
| Phospholipid tested | 20 | 4 | 0.8 |
| Expt 1 | | | |
| None | 3.3 | | |
| Phosphatidyl inositol | 0 | 0 | 0.8 |
| Phosphatidic acid[a] | 3.2 | 3.0 | 3.1 |
| Phosphatidyl choline | 3.4 | 3.4 | 3.4 |
| Phosphatidyl serine | 3.3 | 3.4 | 3.0 |
| Phosphatidyl ethanolamine[a] | 3.5 | 3.2 | 3.3 |
| Cardiolipin | 3.1 | 3.4 | 3.3 |

TABLE 2-continued

Titres of TNF induced by P yoelii exoantigens in the presence of various exogenous phospholipids.

| | μg per ml | | |
|---|---|---|---|
| Phospholipid tested | 20 | 4 | 0.8 |
| Expt 2 | | | |
| None | 3.6 | | |
| Phosphatidyl inositol[a] | 0 | 0 | 0.4 |
| Phosphatidyl choline[a] | 3.6 | 3.6 | 3.6 |
| Phosphatidyl serine[a] | 3.6 | 3.6 | 3.6 |
| Expt 3 | | | |
| None | 4.6 | | |
| Phosphatidyl inositol[a] | 0 | 0 | 1.6 |
| Phosphatidyl serine[a] | 4.6 | 4.6 | 4.6 |

Titres of TNF are log 4 after an initial 1/10 dilution of macrophage supernatants [a]free salt.

None of these phospholipids, even at concentrations of up to 100 μg per ml, stimulated the macrophages to secrete TNF.

Structural requirements of exoantigen inhibitors. To investigate the minimum structure required to inhibit the stimulation of TNF by the P. yoelii exoantigens, macrophage cultures were incubated with a preparation which induced the secretion of 12, 8000 U TNF per ml and various concentrations of either PI, its derivatives inositol monophosphate (IMP) or inositol. Both PI and IMP caused a dose dependent inhibition of TNF production; the results of representative experiments are shown (FIG. 2). Inositol itself did not affect the yield of TNF, indicating that the presence of a phosphate bound to the inositol ring is essential for the exoantigen molecule to interact with the macrophage. This was confirmed by tests with other monophosphate saccharides. Thus, even at 200 μg per ml, the maximum concentration tested, no inhibition was obtained with glucose-1-phosphate, galactose-1-phosphate, mannose-1-phosphate, fructose-1-phosphate, galactosamine-1-phosphate, glucosamine-1-phosphate, or even adenosine triphosphate (ATP) (data not shown). Serological cross-reactions are known to occur between phosphate-containing compounds such as the various phospholipids, lipid A, denatured DNA and lipoteichoic acid (1). Our results indicate, however, that unlike antibody recognition of phosphate esters, recognition by the macrophage receptor of the active moiety of the parasite exoantigens is highly specific, since it possesses a site which can recognise phosphate when bound to inositol but not to other sugars. When an exoantigen preparation was titrated in the presence or absence of 20 μg per ml of IMP, the yield of TNF was reduced by about 16-fold at all dilutions and the inhibition was not overcome at the higher concentrations of the stimulant which appeared to reach a plateau, suggesting that the binding of the inhibitor to this receptor might not be reversible (FIG. 3). As before, inhibition of exoantigen activity was specific, in that neither PI nor IMP, even at concentrations of 20 μg per ml, inhibited TNF induction by LPS (FIG. 4). These results, and our findings of the lack of any effect of the detoxified exoantigens on the yields of TNF stimulated by LPS, also excluded the possibility that any inhibition observed was due to a toxic effect of the inhibitors on the macrophages.

Inhibition of exoantigens of other Plasmodium spp. Since TNF-inducing exoantigens of the rodent parasite P. yoelii and of the human parasites P. falciparum and P. vivax cross-react serologically (5,6), experiments were done to see if preparations which inhibited the activity of exoantigens of P. yoelii were also active against those of the human parasites. The amounts of TNF induced by exoantigens of both P. falciparum and P. vivax decreased in a dose-dependent manner in the presence of partial structures of P. yoelii exoantigens, in this case, produced by lipase digestion (FIG. 5). Furthermore, incubation with PI and IMP also inhibited the induction of TNF by exoantigens of P. falciparum and P. vivax (FIG. 6).

TNF production by macrophages pretreated with inhibitors. The inhibitory effects described above were all observed in experiments in which macrophages were incubated overnight in the presence of both stimulant and inhibitor. To distinguish a possible effect of the inhibitor on the exoantigens themselves from an effect on the cells and to investigate the possibility that the inhibitors acted by blocking cell receptors, macrophages were pretreated with various inhibitors for 30 mins, washed, and then exposed to the exoantigens overnight as usual. Since only small inhibitory effects were detected in pilot experiments, perhaps due to the expression of new receptors, exoantigens were removed from the pretreated macrophages after 1 hr in subsequent experiments and the cells were washed before overnight incubation in fresh medium.

The yields of TNF obtained from macrophages that had been pretreated with a ⅕ dilution of detoxified P. yoelii supernatants, PI or IMP (both at 20 μg per ml) and then incubated with P. yoelii exoantigens were greatly decreased, whereas control cultures pretreated with 50 μg per ml of PE or PC were unaffected (FIG. 7. Again, in contrast to results with exoantigens, pretreatment of the cells with lipase-digested exoantigens did not diminish the amounts of TNF produced in response to LPS (1 μg per ml) (not shown).

Platele Activating Factor inhibitor. Since the PAF antagonist SRI 63-119 has been shown to block a TNF-mediated effect of LPS (38), we examined the effects of the antagonist, 1-O-hexadecyl-2-acetyl -sn-glycero-3-phospho (N,N,N-trimethyl)hexanolamine, on TNF production induced by P. yoelii exoantigens compared with LPS. No distinction was found, as the antagonist caused a dose-dependent inhibition in the yields of TNF obtained in response to both stimulants (FIG. 8). Furthermore, no significant inhibition occurred in response to either when they were incubated with washed macrophages that has been pretreated with 50 μg/ml of inhibitor. These findings also showed that the antagonist did not have a toxic effect on the macrophages.

DISCUSSION

Our most striking finding is that the TNF-inducing activity of molecules released into the medium by erythrocytes infected with P. yoelii, or with the human parasites P. falciparum and P. vivax can be inhibited, clearly and reproducibly, by the simple, chemically defined molecules phosphatidyl inositol and inositol monophosphate and by parasite exoantigens modified to render them non-toxic. These results support our previous conclusion that the active component of the exoantigens of P. yoelii depends upon a phospholipid and provide more information about the nature of this phospholipid.

Two lines of evidence indicate that the inhibitory activity of PI is not medicated through its diacylglycerol component: first, diacylglycerol is present in all the phospholipids tested that had no inhibitory effect and secondly, exoantigens from which it has been removed by lipase digestion are still inhibitory. Furthermore, IMP, an unacylated form of PI, was also inhibitory. Such inhibition occurred when covalently bound phosphate and inositol were present; neither inositol itself nor a number of other monophosphate saccharides were effective. The specificity of this inhibition suggests that an inositol phosphate group must be an integral part of the active structure of the exoantigens.

It has been noted that the lipid chemistry of different species of Plasmodium is remarkably similar and differs considerably from that of erythrocytes (3) and that phospholipids of the parasitophorous vacuole (3) and of the rhoptries of merozoites are discharged at the time of invasion (37). The incorporation of inositide into phosphatidyl inositol has been shown to be accelerated during early schizogony (44). Phosphatidyl inositol is a constituent of several antigens of the parasite, including, for example, a merozoite surface antigen (20), forming an essential part of the glycosyl phosphatidyl inositol (GPI) anchor that attaches some proteins to surface membranes (reviewed in 17 and 42). We do not know if the inositol phosphate-containing portion of the exoantigen is covalently bound to a particular protein antigen or merely associates with protein because of its hydrophobic properties but there is reason to believe that it is not a GPI anchor. Thus, nitrous acid deamination of molecules containing these anchors liberates free PI (17,42) and we have shown both that PI does not induce TNF production and that the TNF-inducing activity of the exoantigens is unaffected by deamination. Furthermore, the presence of glucosamine is diagnostic for GPI anchors and they generally contain mannose. Our failure to inhibit the activity of the exoantigens using either glucosamine-1-phosphate or mannose-1-phosphate (or using glucosamine or mannose, data not given, suggests that these sugars if present are not a necessary part of the antigen ligand; we have also showed (data not given) that sugar moieties are not necessary for exoantigen induction of TNF. Inositol monophosphate also inhibits the activity of phosphatidyl inositol glycans (PI-Gs) which mimic the action of insulin on adipocytes (32), probably by competing for receptors. However, in contrast to the parasite exoantigens, glucosamine and mannose also inhibit the activity of the PI-Gs, and deamination by nitrous acid abolishes the insulin-mimicking effect (17).

The inhibitory effect of PI, IMP and the detoxified exoantigens on the TNF-inducing activity of the exoantigens might be explained in two ways: the inhibitors might pass across cell membranes directly and thus inhibit a second messenger system but our findings indicate that this would have to be one which is activated in macrophages stimulated by exoantigens but not by LPS. Alternatively, they may act by competing for specific receptors on the macrophage. The fact that detoxified exoantigens were inhibitory, whether they had been dephosphorylated or de-O-acylated by lipase digestion, suggests that there may be at least two binding sites on the macrophage receptor whose occupancy leads to inhibition: one depending on the presence of phosphorus and one not. For the exoantigens to induce the production of TNF, however, ester-linked acyl chains must also be present (data not shown). We can only speculate as to whether they bind to a third site on the receptor or act on the pathway which leads to the synthesis of TNF by some other route.

Cytokine production by LPS is also abolished by deacylation, and inactive endotoxin derivatives block TNF production (26) and B cell mitogenesis (16) by the active molecule. It is noteworthy that the detoxified exoantigens, PI and IMP did not block the induction of TNF by LPS, confirming our suggestion (41) that the exoantigens and LPS stimulate macrophages via different receptors. The PAF antagonist inhibited TNF induction by both stimulants when incubated with them, but not when used to pretreat macrophages before addition of the stimulants, suggesting that PAF is generated as a common second messenger.

Macrophages bear several classes of scavenger receptor which have affinities for oxidized and acetylated low density lipoproteins (LDL) and which have a broad binding specificity (10, 25). The binding of oxidized LDL to mouse macrophages is inhibited by liposomes containing acidic phospholipids such as PE, PS and PI, and it appears that at least two scavenger receptors recognise these molecules (33). This suggested to us that the inositol phosphate-containing exoantigens might bind to these receptors. We found that exoantigen-induced TNF secretion was indeed inhibited by oxidised by not native LDL. Like Hamilton et al. (22), we found that oxidized LDL itself did not induce peritoneal macrophages to secrete TNF, and that it did not inhibit the TNF-inducing activity of LPS. However, in preliminary experiments we could not detect significant inhibition of exoantigen activity by such scavenger receptor ligands as fucoidan, dextran sulphate and polyinosinic acid and furthermore macrophages pretreated with oxidized LDL still responded to stimulation by the exoantigens. While such findings depend greatly upon the experimental conditions used, the possibility that oxidised LDL was inhibitory because it formed a complex with the exoantigens should be considered. Work with endotoxin has shown that the binding of the LPS derivative lipid $IV_A$ to a mouse macrophage cell line is mediated by a scavenger receptor since it is inhibited by acetylated LDL (23). Binding to this receptor did not stimulate macrophages to secrete TNF, although others have reported that acetylated LDL at very high concentrations stimulated human monocytes to secrete a short burst of TNF that had disappeared from the medium by 24 hr (4). Since scavenger receptor ligands inhibited hepatic uptake of lipid $IV_A$ in mice, it was suggested that such a receptor may be involved in the clearance and detoxification of endotoxin in vivo (23).

The toxic properties of the exoantigens may explain some of the clinical complications of malaria and, if so, modified exoantigens might form the basis of an anti-disease vaccine (34). The findings reported here provide another approach to the management of malaria. The toxicity of infection might be reduced specifically by administration of exoantigen partial structures, or by other simpler inhibitors. Thus, in addition to measures designed to counteract the harmful effects of cytokines, such as the administration of monoclonal antibodies or of cytokine inhibitors, this kind of therapy, which should act earlier in the toxigenic pathway, might prevent the production of excess TNF and perhaps of other cytokines or damaging processes that might be activated by these parasite exoantigens.

References

1. Alving C. R. 1986. Antibodies to liposomes, phospholipids and phosphate esters. Chem. Phys. Lipids 40: 303–314.
2. Aschauter, H., A. Grob, J. Mildenbrandt, E. Schutze and P. Stutz. 1990 Highly purified lipid X is devoid of immunostimulatory activity. Isolation and characterization of immunostimulating contaminants in a batch of synthetic lipid X. J. Biol. Chem. 265: 9159–9164.
3. Bannister L. H. and G. H. Mitchell. 1986 Lipidic vacuoles in *Plasmodium knowlesi* erythrocytic schizonts. J. Prozozool. 33: 271–275.
4. Barath P., J. Cao and J. S. Forrester. 1990. Low density Lipoprotein activates monocytes to express tumor necrosis factor. FEBS. 227: 180–184.
5. Bate, C. A. W., J. Taverns, A. Dave and J. H. L. Playfair. 1990. Malaria exoantigens induce T-independent antibody that blocks their ability to induce TNF. Immunology, 70: 315–320.

6. Bate, C. A. W., J. Taverns, N. D. Karunaweera, K. N. Mendis and J. H. L Playfair. 1992 Serological relationship of TNF-inducing exoantigens of *P. falciparum* and *P. vivax*. Infect. Immun. Submitted.
7. Bate, C. A. W., J. Taverns and J. H. L Playfair. 1988. Malarial parasites induce tumour necrosis factor production by macrophages. Immunology. 64: 227–231.
8. Bate, C. A. W., J. Taverns and J. H. L. Playfair 1989. Soluble malarial antigens are toxic and induce the production of tumour necrosis factor in vivo. Immunology. 66: 600–605.
9. Bate C. A. W., J. Taverns, E. Roman, C. Moreno and J. H. L. Playfair.1992. TNF induction by malaria exoantigens depends upon phospholipid. Immunology. In Press.
10. Brown M. S. and J. L. Goldstein 1983. Lipoprotein metabolism in the macrophage: implication for cholesterol deposition in atherosclerosis. Annu. Rev. Biochem 52: 223–261.
11. Cerami A. and B. Beutler 1988. The role of cachectin/TNF in endotoxic shock and cachexia. Immunol. Today, 9: 28–31.
12. Chang, S. W., C. O. Feddersen, P. M. Henson and N. F. Voelkel.1987. Platelet-activating factor mediates hemodynamic changes and lung injury in endotoxin-treated rats. J. Clin. Invest. 79: 1495–1509.
13. Clark I. A. 1978. Does endotoxin cause both the disease and parasite death in acute malaria and babesiosis? Lancet (ii) 75–77.
14. Clark I. A., G. Chaudhri and W. B. Cowden. 1989. Roles of tumour necrosis factor in the illness and pathology of malaria. Trans. Roy. Soc. Trop. Med.& Hyg. 83: 436–440.
15. Dinarello, C. A., J. G. Cannon, S. M. Wolff, H. A. Berheim, B. Beutler, A. Cerami, I. S. Figari, M. A. Palladino Jr, and J. V. O'Connor 1986. Tumor necrosis factor (Cachectin) is an endogenous pyrogen and induces production of interleukin 1. J. Exp. Med.163: 1433–1450.
16. Erwin, A. L., R. E. Mandrell and R. S. Munford.1991 Enzymatically deacylated Neisseria lipopolysaccharide (LPS) inhibits murine splenocyte mitogenesis induced by LPS. Infect. Immun. 59: 1881–1887.
17. Ferguson M. A. J. and A. F. Williams.1988. Cell-surface anchoring of proteins via glycosyl phosphatidylinositol structures. Ann. Rev. Biochem. 57: 285–320.
18. Freeman R. R. and A. A. Molder, 1983. Characteristics of the protective response of BALB/c mice immunized with a purified *Plasmodium yoelii* Schizont antigen. Clin. Exp. Immunol. 54: 609–616.
19. Grau G. E., T. E. Taylor, M. E. Molyneux, J. J. Wirima, P. Vassalli, M. Hommel and P. -H. Lambert.1989. Tumor necrosis factor and disease severity in children with falciparum. N. Eng. J. Med.,320: 1586–1591.
20. Haldar K., M. A. J. Ferguson and G. A. M. Cross. 1985. Acylation of a *Plasmodium falciparum* merozoite surface antigen via sn-1,2-diacyl glycercl. J. Biol. Chem.260: 4969–4974.
21. Halonen M., J. D. Palmer, C. Lohman, L. M. McManus and R. N. Pinckard. 1980. Respiratory and circulatory alterations induced by acetyl glyceryl ether phosphorylcholine, a mediator of IgE anaphylaxis in the rabbit. Am. Rev. Resp. Dis. 122: 915–924.
22. Hamilton, T. A., G. Ma and G. M. Chisolm. 1990. Oxidized low density lipoprotein suppresses the expression of tumour necrosis factor-$\alpha$ mRNA in stimulated murine peritoneal macrophages. J. Immunol. 144: 2343–2350.
23. Hampton, R. Y., D. T. Golenbock, M. Penman, M. Krieger and C. R. H. Raetz. 1991. Recognition and plasma clearance of endotoxin by scavenger receptors. Nature (Lond). 352: 242–344.
24. Kern P., C. J. Hemmer, J. van Damme, H. -J. Gruss and M. Dietrich.1989. Elevated tumor necrosis factor $\alpha$ and interleukin-6 serum levels as markers for complicated *Plasmodium falciparum* malaria. Amer. J. Med. 57: 139–143.
25. Kodama T., M. Freeman, L. Rohrer, J. Zabrecky, P. Matsudaira and M. Krieger. 1990. Type I macrophage scavenger receptor contains $\alpha$-helical and collagen-like coiled coils. Nature (Lond.) 343: 531–535.
26. Kovach N. L., E. Yee, R. S. Munford, C. R. H. Raetz and J. M. Harlan, 1990. Lipid $IV_A$ inhibits synthesis and release of tumor necrosis factor induced by lipopolysaccharide in human whole blood ex vivo. J. Exp. Med.172: 77–84.
27. Kwiatkowski D., J. G. Cannon., K. R. Manogue, A. Cerami, C. A. Dinarello and B. M. Greenwood. 1989. Tumour necrosis factor production in Falciparum malaria and its association with schizont rupture. Clin. Exp. Immunol. 77: 361–366.
28. Kwiatkowski D., A. V. S. Hill, I. Sambou, P. Twumasi., J. Castracane, K. R. Manogue, A. Cerami, D. R. Brewster and B. M. Greenwood 1990. TNF concentration in fatal cerebral, non-fatal cerebral, and uncomplicated *Plasmodium falciparum* malaria. Lancet 336: 1201–1204.
29. Kwiatkowski D., M. E. Molyneux, F. Pointaire, N. Curtis, N. Klein, M. Smit, R. Allan, S. Stephens, G. E. Grau, P., Holloway, D. R. Brewster and B. M. Greenwood. 1992. Monoclonal anti-TNF antibody in the treatment of childhood cerebral malaria. New Engl. J. Med. Submitted.
30. Lam, C., J. Kildebrandt, E. Schutze, B. Rosenwirth, R. A. Proctor, E. Liehl and P. Stutz. 1991. Immunostimulatory, but not antiendotoxin, activity of lipid X is due to small amounts of contaminating N,O-acylated disaccharide-1-phosphate: in vitro and in vivo revaluation of the biological activity of synthetic lipid X. Infect. Immun. 59: 2351–2358.
31. Lasfargues A. and Chaby R. 1988. Endotoxin-induced tumor necrosis factor (TNF): selective triggering of TNF and interleukin-1 production by distinct glucosemine-derived lipids. Cell. Immunol. 115: 165–178.
32. Machicae, F., J. Mushack, E. Seffer, B. Ermel and H-U. Haring, 1990. Mannose, glucosamine and inositol monophosphate inhibit the effects of insulin on lipogenesis. Biochem. J. 266: 909–916.
33. Nishikawa K., H. Arai and K. Inoue. 1990. Scavenger receptor-mediated uptake and metabolism of lipid vesicles containing acidic phospholipids by mouse peritoneal macrophages. J. Biol. Chem. 265: 5226–5231.
34. Playfair, J. H. L., J. Taverne, C. A. W. Bate and J. B. de Souza 1990. The malaria vaccine: anti-parasite or anti-disease? Immunol. Today. 11: 25–27.
35. Pollack, M., A. A. Raubitchek and J. W. Larrick. 1987. Human monoclonal antibodies that recognise conserved epitopes in the core-lipid A region of lipopolysaccharides. J. Clin. Invest. 79: 1421–1430.
36. Proctor, R. A., J. A. Will, K. E. Burhop and C. R. H. Raetz. 1986. Protection of mice against lethal endotoxemia by a lipid A precursor. Infect. Immun. 52: 905–907.
37. Stewart M. J., S. Schulman and J. P. Vanderberg. 1986. Rhoptry secretion of membranous whorls by *Plasmodium falciparum* merozoites. Amer. J. Trop. Med. Hyg. 35: 37–44.
38. Sun X, and W. Hsueh. 1988. Bowel necrosis induced by tuor necrosis factor in rats is mediated by platelet-activating factor. J. Clin. Invest. 81: 1328–1331.

39. Taverne J., C. A. W. Bate, D. Kwiatkowski, P. H. Jakobsen & J. H. L. Playfair. 1990. Two soluble antigens of *P. falciparum* induce TNF release from macrophages. Infect. & Immun. 58: 2923–2928.
40. Taverne J., C. A. W. Bate & J. H. L. Playfair. 1990. Malaria exoantigens induce TNF, are toxic and are blocked by T-independent antibody. Immunol. Letters, 25: 207–212.
41. Taverns, J., C. A. W. Bate, D. A. Sarkar, A. Meager, G. A. W. Rook and Playfair, J. H. L. 1990. Human and murine macrophages produce TNF in response to soluble antigens of *Plasmodium falciparum*. Parasite. Immunol. 12: 33–43.
42. Thomas J. R., R. A. Dwek and T. W. Rademacher. 1990. Structure, biosynthesis and glycosylphosphatidylinositols. Biochem. J. 29: 5413–5422.
43. Tracey, K. J., Fong, Y., Hesse, D. G., Manogue, K. R., Lee, A. T., Kuo, G. C., Lowry, S. F. and Cerami, A. 1987. Anti-cachectin/TNF monoclonal antibodies prevent septic shock during lethal bacteraemia. Nature. 330. 662–666.
44. Vial, H. J., M. J. Thuet and J. R. Philippot. 1982. Phospholipid biosynthesis in synchronous *Plasmodium falciparum* cultures. J. Prozozool. 29: 258–263.

Example 2

Abstract

Phospholipid-containing antigens of malaria parasites stimulate macrophages to secrete tumour necrosis factor (TNF), induce hypoglycaemia and are toxic to mice. This TNF induction is inhibited by antisera made against the antigens, the inhibitory activity of which can be removed specifically by adsorption to phosphatidylinositol (PI) liposomes. Although the same was true of antisera made against PI, the inhibitory activity of antisera made against some other phospholipids appeared to be directed against a common determinant, probably the phosphate ester head group. We have shown previously that the activity of all the antisera was associated mainly with IgM and was not boosted by repeated injections of the antigens. To try and induce a secondary response against the parasite antigens using non-toxic molecules, mice were immunized with various phosphorylated compounds coupled to keyhole limpet haemocyanin (KLH). Three injections of PI-KLH or of phosphatidylserine (PS) coupled to KLH induced significantly higher titres of inhibitory antibody than one; furthermore, the inhibitory activity was mainly in the IgG fraction. The antisera does not inhibit TNF induction by LPS or lipoteichoic acid. However antisera against PS-KLH, though not PI-KLH, inhibited the induction of TNF by the phospholipid, platelet-activating factor (PAF). These antisera, and antisera from mice immunized with phosphothreonine or galactosamine-1-phosphate conjugated to KLH, contained inhibitory antibodies of differing specificities. Mice immunized with PI-KLH, PS-KLH or phosphothreonine-KLH did not develop hypoglycaemia when challenged with the parasite toxic antigens. These results indicate that the antigenicity of non-toxic analogues can be dramatically enhanced by coupling to a protein carrier.

Introduction

Figure 1A:
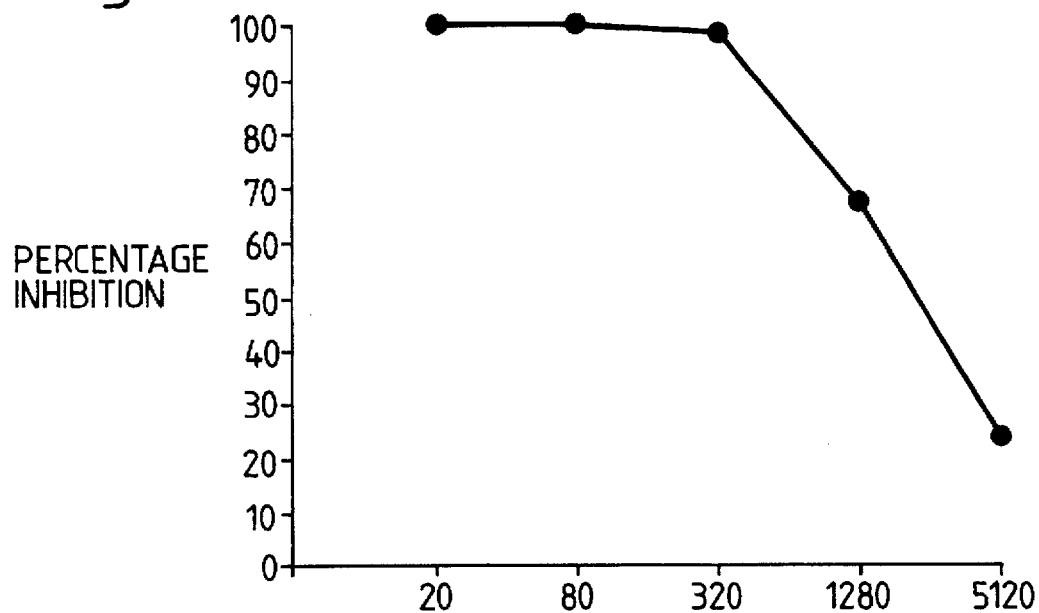
Figure 1B:
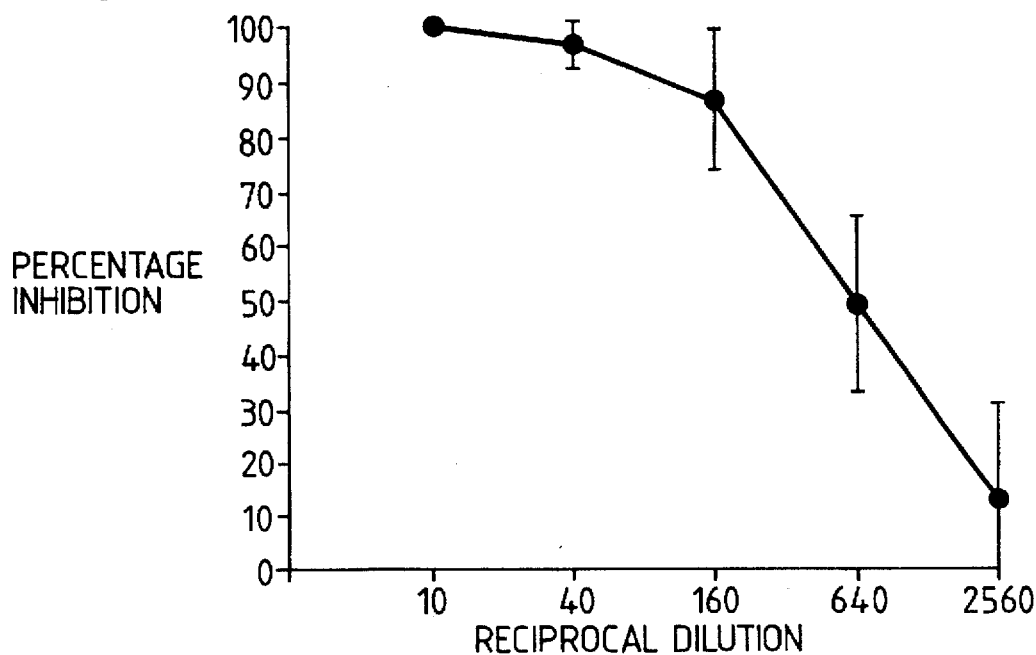
Figure 2:
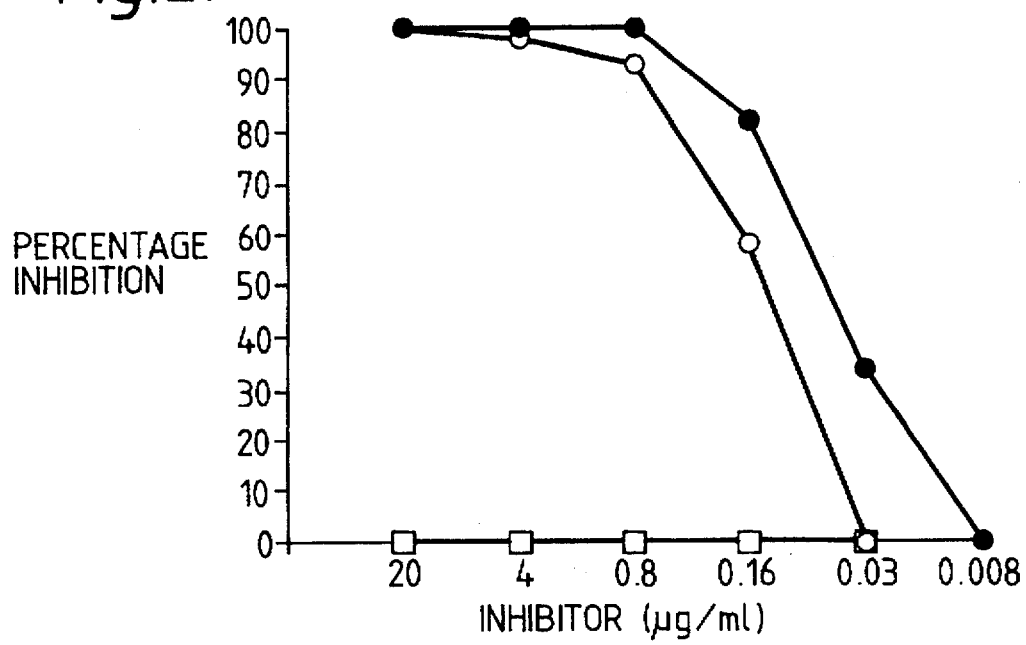
Figure 3:
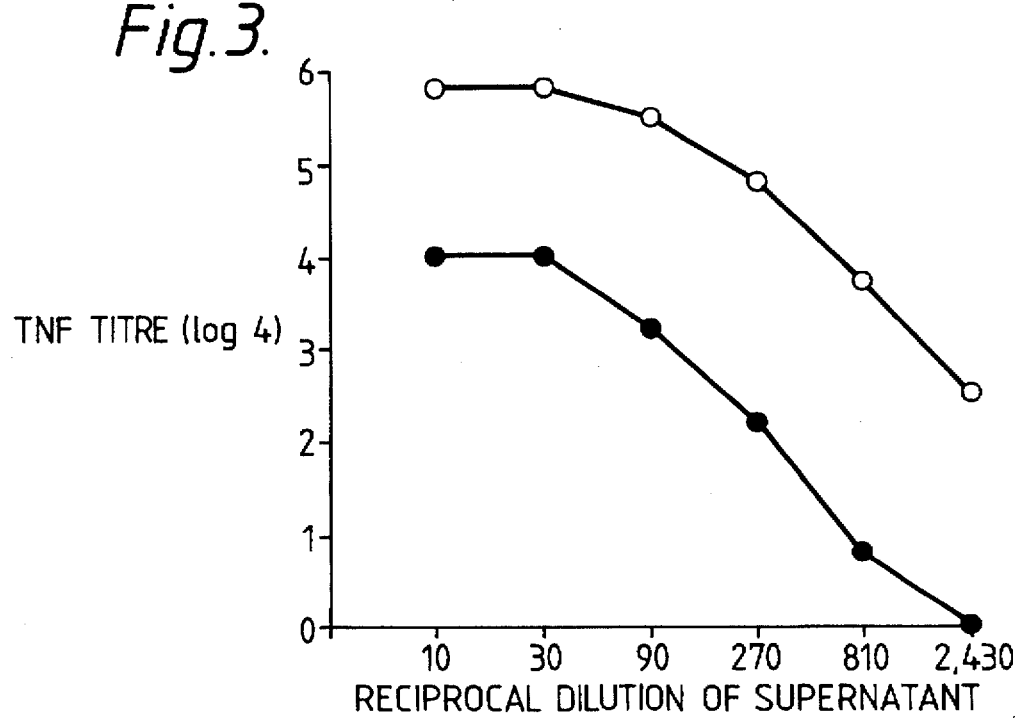
Figure 6A:
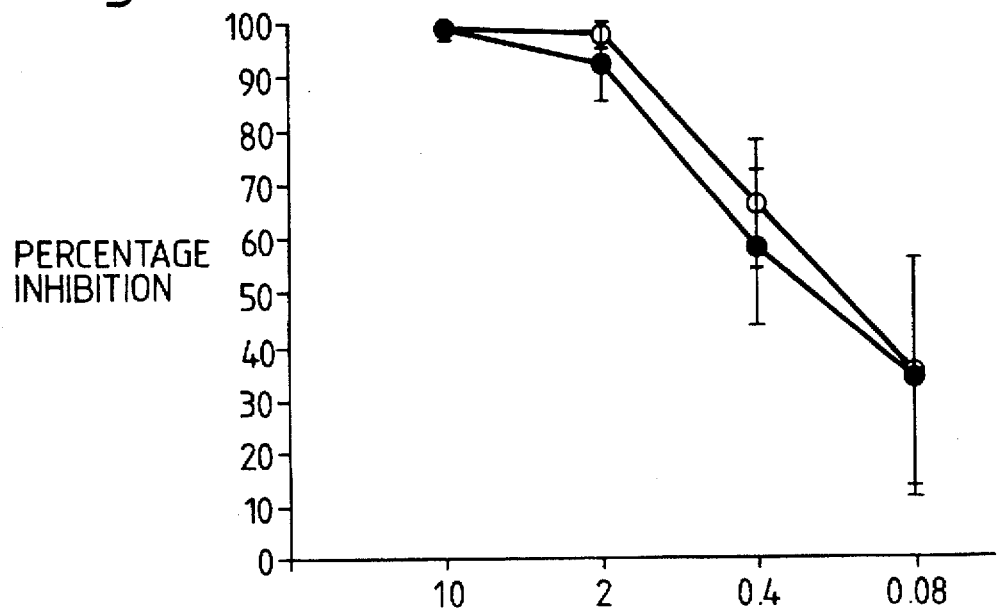
Figure 6B:
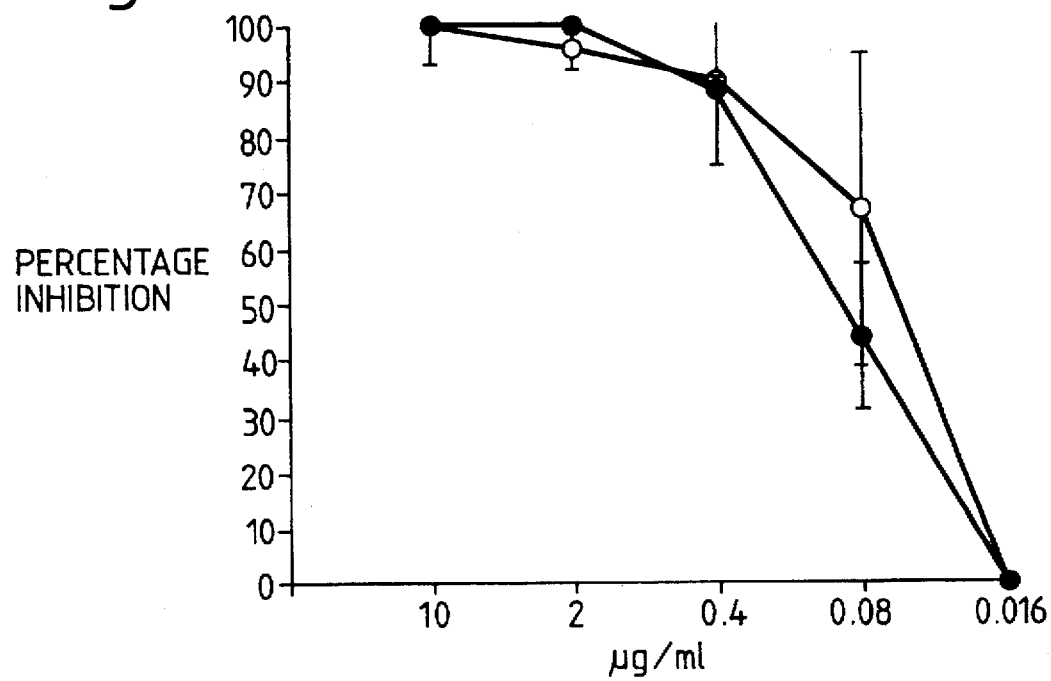
Figure 7:
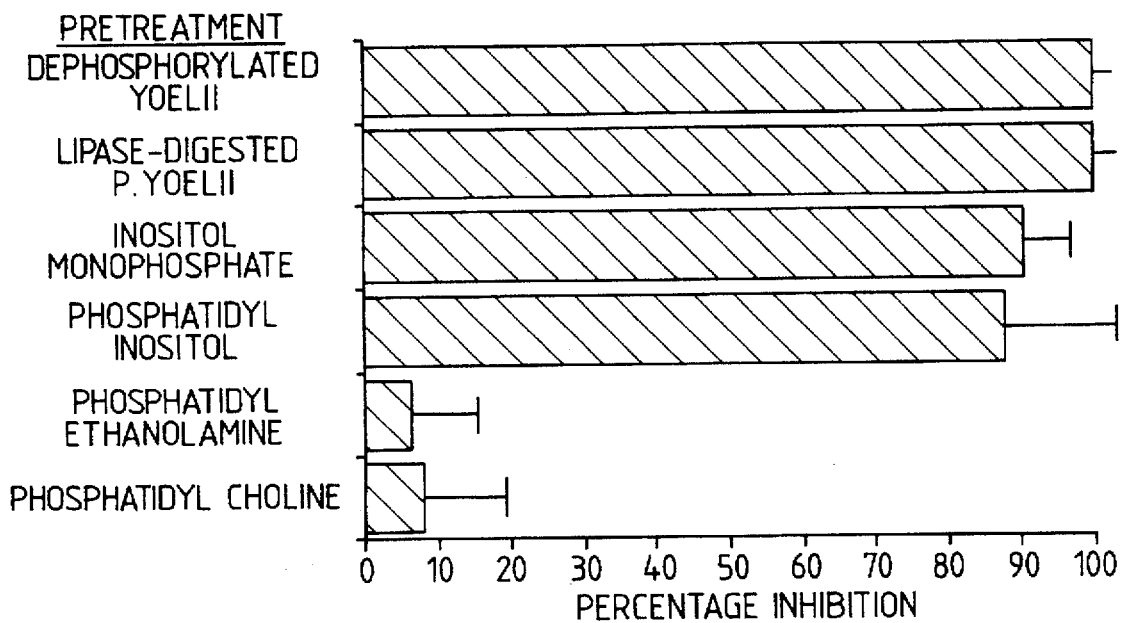
Figure 8:
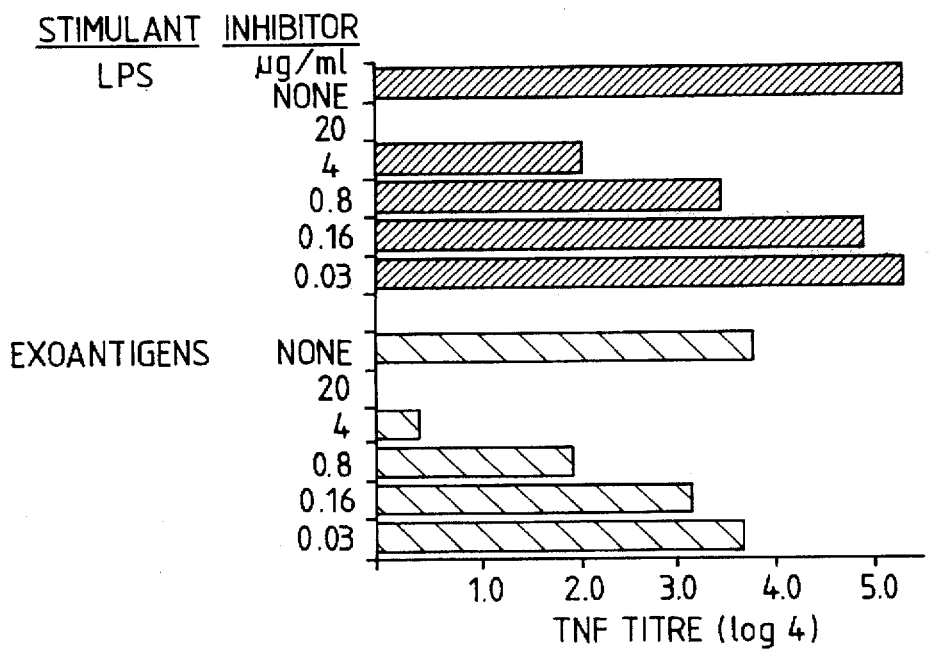

While tumour necrosis factor (TNF) is widely accepted as playing an important role in septic shock (1), its possible involvement in the illness and pathology of malaria has only recently been recognised, the subject has been well reviewed by Clark and his co-workers (2). In patients infected with *Plasmodium falciparum*, increased levels of circulating TNF are associated with the severity of the disease (3,4), and especially with death from cerebral malaria (5). Among its many properties, TNF can cause various changes in vascular endothelium. For example, it can increase the expression of adhesion molecules such as ICAM-1 (6), one of the molecules that may be concerned in the attachment of parasitized erythrocytes to the endothelium of brain capillaries (7). It can also increase the production of nitric oxide from endothelial cells (8), which if it occurred in the cerebral capillaries might alter the activity of underlying neurons (9).

Substances released by both rodent and human malaria parasites stimulate mouse macrophages (10) and human monocytes (11,12) to secrete TNF. Furthermore, those from both rodent parasites and *P. falciparum* are toxic, in that they kill mice sensitised to TNF by treatment with D-galactosamine (13), suggesting that they might be involved in the pathology of infection. We have shown that the induction of TNF by these parasite antigens depends upon a phospholipid component (14) and that this activity can be inhibited by the addition of phosphatidylinositol (PI) or inositol monophosphate (IMP), suggesting that the active moiety contains PI (15); furthermore, the inhibitory activity of antibodies against these antigens was specifically adsorbed by liposomes containing PI (16).

We have previously referred to these TNF-inducing phospholipid-containing antigens as "exoantigens", as they are present in the medium of cultures of *P. falciparum* and in supernatants from rodent malarial parasites incubated overnight at 37°. Since they are also present in intact, as well as lysed, parasitized erythrocytes, (14), it would seem more correct to refer to then as toxic antigens.

Immunization with the toxic antigens of *P. yoelii* prevents mortality in groups of mice treated with D-galactosamine, before challenge with the antigens, and protection is associated with antibody that inhibits the antigen-induced TNF secretion in vitro (13). We therefore proposed that these antigens might form the basis of an anti-disease vaccine (17). Our finding that the TNF-inducing antigens from different rodent parasites and from *P. falciparum* and *P. Vivax* are serologically related (18, 19) suggests that they are conserved. However, since they are not only toxic but give rise mainly to T-independent antibody which is predominantly IgM (19), the immunogen of choice would probably need to be rendered non-toxic and modified so as to generate immunological memory.

We had found that a number of compounds, including PI and its derivative IMP and phosphatidylserine (PS) (in liposomal form), none of which stimulate TNF secretion by macrophages, also induce the production of inhibitory antibodies; again these were predominantly IgM and their titres were not enhanced repeated injections (16). A memory response has, however, been induced to the organophosphorus neurotoxin soman, coupled to keyhole limpet haemocyanin (KLH) (20). Therefore, to try and induce high titre inhibitory antibody and immunological memory, using a non-toxic phospholipid as an immunogen, we coupled PI, PS and some other phosphorylated compounds to KLH immunized mice with them and investigated their antibody responses.

Hypoglycaemia is known to be associated with severe malaria (21) and we have shown that supernatants from blood stage *P. yoelii* induce hypoglycaemia in mice, with a time course different from that seen after injection of insulin (22). The antigens which precipitate a fall in blood glucose levels in vivo resemble those which induce the production of TNF in vitro in a number of ways, suggesting that they too might be PI-containing phospholipids (22). However a monoclonal antibody which neutralised the activity of murine TNF did not block the hypoglycaemic response to the toxic antigens. Since mice immunized with the antigens were protected against the antigen-induced hypoglycaemia, we have also examined mice immunized with some of the KLH conjugates to see if they too were protected.

Materials and Methods

Mice

Antisera were generated in outbred female mice which were at least 6 weeks old (Tuck No1: A. Tuck & Sons, Battlesbridge, Essex and MF-1: Harlan Olac, Bicester, Oxon). Hypoglycaemia experiments were done in (C57 B1×Balb/c) F1 females at least 10 weeks old.

Toxic antigens

From *P. yoelii* YM (obtained from D. Walliker, Edinburgh University, Edinburgh, UK): These were prepared as previously described (14), by incubating washed parasitized erythrocytes, obtained from mice with high parasitaemia, at $10^8$ parasites/ml in PBS overnight on a roller at 37°. Next day supernatants were collected, centrifuged, boiled for 5 min, and centrifuged again. There were then incubated for 24 h at 37° C. in 10 µg per ml of pronase E (Sigma), since TNF-inducing activity is not associated with protein but is enhanced by its removal (14). They were then boiled and dialysed against PBS, when no protein was detectable by BioRad assay (<1 µg per ml). Before use, they were mixed with 5 µg/ml of polymyxin B-agarose (Sigma) to remove any endotoxin, centrifuged, passed through a 0.2 µm filter and stored at 4° C.

From *P falciparum*

These were obtained from cultures of *P. falciparum* maintained in Group O erythrocytes in RPMI 1640 containing 10% A⁻ human serum. Schizonts were enriched by plasmagel, washed 3 times, resuspended at $5×10^-$ per ml in serum-free RPMI 1640 and incubated overnight at 37° C. Next day the cultures were vortexed for 30 secs, centrifuged at 10,000×g for 10 min and the supernatant collected and stored at 4° C. for use.

Stimulation assays: (i) using mouse peritoneal macrophages

The cells were prepared as described (14). Briefly, they were collected from mice given 1 ml of 4% thioglycollate (Difco) i.p. 3–5 days previously, using Hank's BSS (Flow Laboratories) containing 1 U/ml of heparin and 5 µg/ml of polymyxin B (Sigma). Washed cells were suspended in 5% foetal calf serum (FCS) in RPMI 1640 containing 5 µg/ml polymyxin B, at $1×10^-$ viable cells per ml and 0.1 ml volumes were dispensed into wells of 96-well microtitre plates (Nunc) and incubated for 1–2 hr.

Adherent cells were incubated for 30 min with an equal volume of medium containing 2 µg/ml indomethacin (Sigma) which was then replaced by 0.2 ml volumes of serial dilutions of the stimulants to be tested, made in RPMI 1640 containing polymyxin B [except in the case of lipopolysaccharide (LPS) controls] and the cultures were incubated overnight. Next day, supernatants were collected for assay for TNF; they were stored at −20° in medium containing 5% FCS and 1 µg/ml of emetine (Sigma). Cultures incubated with serial dilutions of LPS (phenol extract of *Escherichia Coli* 055:B5 Sigma) and with medium alone were included in every experiment as positive and negative controls for the capacity of the macrophages to yield TNF. (ii) using human peripheral blood mononuclear cells (PBMNC)

Heparinised blood was mixed with an equal volume of saline and mononuclear cells were isolated on Lymphprep (Nyegaard, Oslo, Norway). They were washed twice, resuspended in serum free MEM at $1×10^5$ cells per ml, and dispensed in 100 µl volumes in flat bottomed 96 well microtitre plates. 100 µl per well of MEM or antiserum dilutions made in MEM, were then added, followed by 100 µl of stimulant. The plates were incubated overnight at 37° C. and the supernatants were then harvested and assayed for TNF.

Antisera

To compare the inhibitory activity of antiserum to IMP against toxic antigens of both *P. falciparum* and *P. yoelii* tested on both human monocytes and mouse macrophages, groups of mice were injected i.p. with 200 µg of IMP (Sigma), bled 12 days later and their serum pooled. For the induction of secondary responses, various phosphorylated compounds were conjugated to protein by mixing 400 µg/ml in PBS at pH 5.0 with 400 µg/ml of KLH (Calbiochem) on ice. They were: PI (from soya bean or bovine liver, Sigma), PS (from bovine brain; Sigma), O-phospho-DL-threonine (Sigma) and D-galactosamiine-1-phosphate (Sigma). They were then mixed with an equal volume of ice cold 150 mM 1-ethyl-3(3-dimethylaminopropyl)-carbodiimide (EDC: Sigma), vortexed and left for 1 hr on ice, when excess EDC was quenched by addition of lysine (Sigma) to 1 mg/ml, and they were then dialysed. Groups of mice were injected i.p. at fortnightly intervals with 0.5 ml (which would have contained 100 µg of the phosphorylated compound if it had all been conjugated to the KLH) and they were bled 12 days after the last injection. Other groups of mice were also immunized similarly with 3 injections of 200 µg PI or 0.5 ml of *P. falciparum* toxic antigens. Antisera were heat-inactivated at 56° C. and before use in the human PBMNC system they were adsorbed with human erythrocytes. They were titrated for their ability to block the induction of TNF by the parasite toxic antigens by mixing equal volumes of serial dilutions made in serum free medium with one dilution of an antigen preparation, chosen so that it was on the linear portion of the dose response curve, before addition to macrophages. It was found to be important to perform titrations using cells that had been washed in serum free medium. Titres are defined as the reciprocal of the dilution that reduced the amount of TNF produced by 50 percent. (Direct comparisons cannot be made between the inhibitory titres of the antisera against the different compounds, however, as the efficiency of conjunction was not determined, so that differences between the magnitude of responses might reflect concentration of immunogen rather than immunogenicity).

Determination of Ig isotypes

Antisera were depleted of IgG or IgM on isotype-specific agarose (Sigma) and the antibody was eluted with 0.1M glycine HCl at pH 2.5 into 1.0M Tris buffer at pH 8, dialysed against PBS and returned to the original volume.

Adsorption by liposomes

Multilamellar dehydration-rehydration vesicles (16) were kindly supplied by Prof. G. Gregoriadis (School of Pharmacy, London University). Antisera diluted 1/50 in RPMI were incubated for 1 hr at room temperature with 2 mg/ml of the liposomes, which were then deposited by centrifugation; this was repeated twice.

Cytotoxicity assay for murine TNF

Samples were assayed colorimetrically by their cytotoxicity for L929 cells as described previously (14). Serial dilutions were tested in duplicate, in 0.1 ml volumes/well, in RPMI containing 1 µg/ml emetine. One unit is defined as that causing 50% cell destruction.

ELISA assay for human TNF

Microtitre plates (Nunc Immunoplate Maxisorp) were coated overnight at 37° C. with 5 µl/well of carbonate buffer pH 9.0 containing 5 µg/ml of a monoclonal antibody against human TNF (CB0006; a kind gift from Celltech, UK). The plates were washed in PBS containing 0.02% Tween 20 and then incubated for 2 hr at 37° C. with 50 µl/well of the samples to be tested. They were then washed again and incubated for 1 hr at 37° C. with 50 µl/well of a rabbit antiserum against human TNF (Endogen) diluted to 1 µg/ml in PBS/Tween containing 2% normal goat serum. They were then washed and incubated for 1 hr at 37° with goat anti-rabbit Ig conjugated to alkaline phosphatase (Sigma), when they were washed and the colour developed with p-nitrophenylphosphate tablets a 1 mg/ml (Sigma) in diethanolamine buffer pH10.5 and the OD 405 nm read on a Dynatech Microelisa Autoreader.

Measurement of blood glucose

Glucose concentrations were determined from a drop of tail blood from the mice, using Glucostix and an Ames Glucometer (Miles Lid, Stoke Poges, Slough, UK) according to the manufacturer's instructions (22). Results are expressed as means (±SD) of groups of at least 3 mice.

Other Reagents

Lpoteichoic acid from *Staph. aureus* was obtained from Sigma and platelet activating factor (PAF) from Calbiochem.

Results

Figure 9:
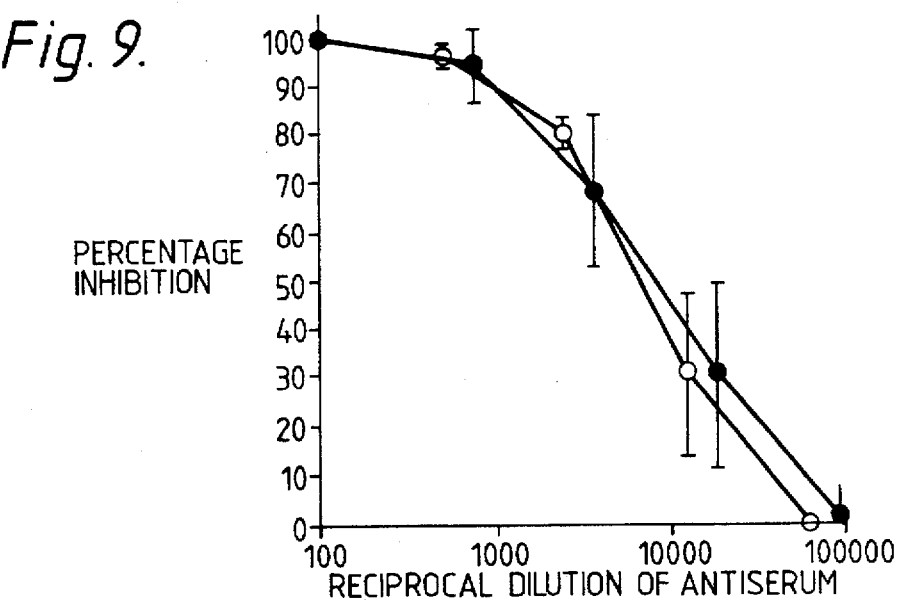

Mouse macrophages and human monocytes secrete TNF in response to toxic malaria antigens both rodent and human parasites (11) and this TNF production can be inhibited by antisera against the toxic antigens from either source, since they cross-react (18,19) as well as by antisera made against PI and IMP (16). When we compared the inhibitory activity of 5 batches of antiserum against IMP, titrated numerous times using preparations of either *P. falciparum* or *P. yoelii* in human or mouse cells respectively, we found that the inhibitory titres were not significantly different (FIG. 9). Therefore, in the work described below we have pooled results obtained from the two systems.

Inhibitory activity of antiserum against PI conjugated to KLH

Figure 10A:
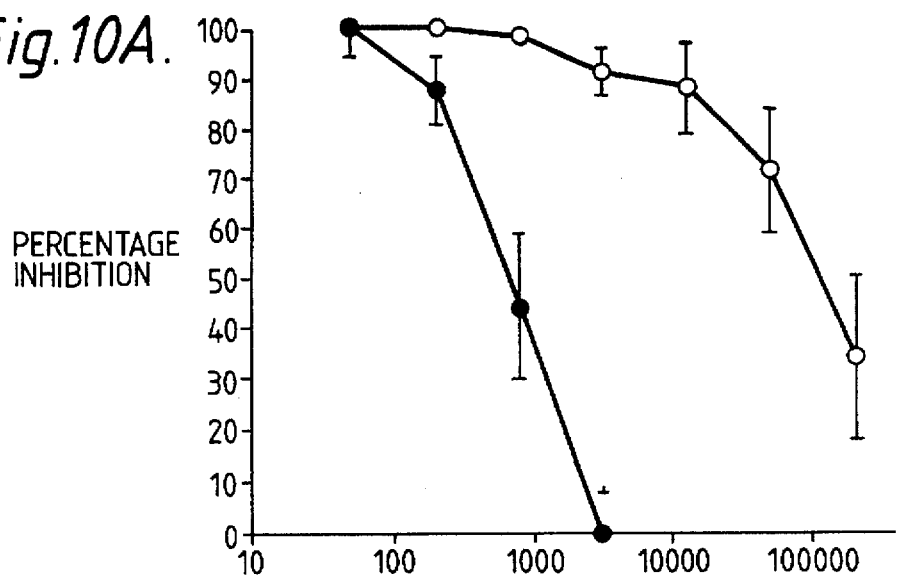
Figure 10B:
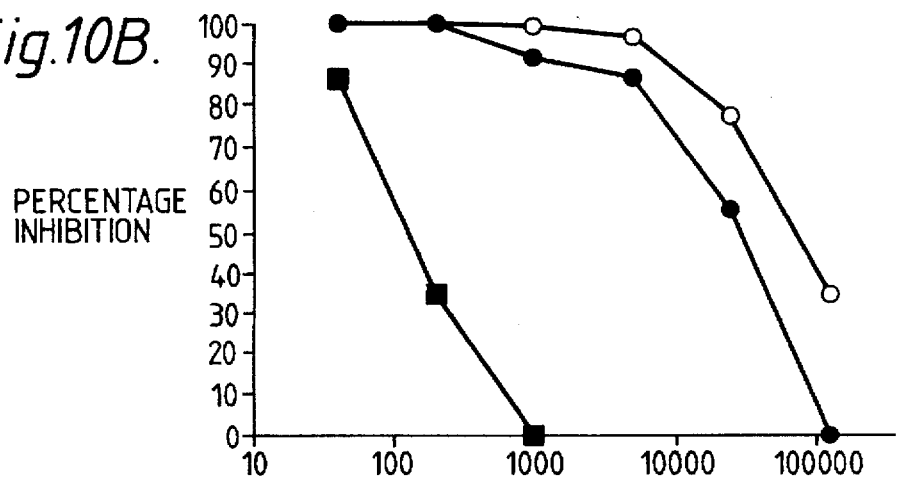

Antisera obtained after 3 injections of PI-KLH were about 100 times more effective at blocking the induction of TNF by the toxic antigens than those obtained after one injection (FIG. 10a). In contrast to our findings with antisera against the toxic antigens of *P. yoelii*, *P. falciparum* and *P. vivax* (18,19) and with antisera against IMP (16) and unconjugated PI (unpublished work), in which the activity was predominantly associated with IgM most of the activity was now found to reside in the IgG fraction, although IgM antibodies were still detectable (FIG. 10b).

Figure 10C:
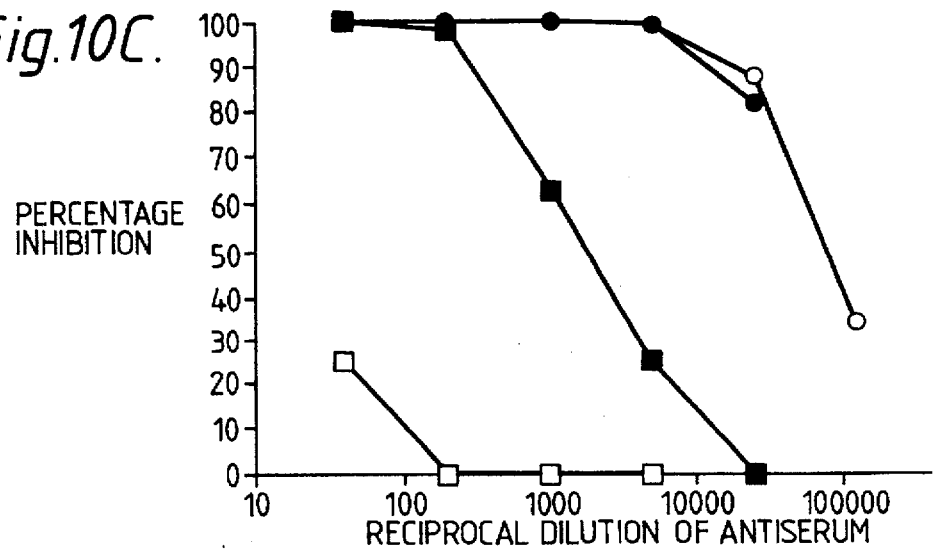

We had previously found that there are at least two kinds of inhibitory antibody, one generated in response to the parasite toxic antigens, or to PI or IMP, which specifically recognises PI in liposomal form, and another which is less specific and seems to recognise a broad range of phospholipids (16). To investigate the specificity of the antibody present after 2 injections of PI-KLH we adsorbed the antiserum with various kinds of liposome (FIG. 10c). The inhibitory activity was not adsorbed by PC, was reduced by PS, and was completely lost after incubation with PI liposomes.

Inhibitory activity of antiserum against conjugated to KLH

Figure 11A:
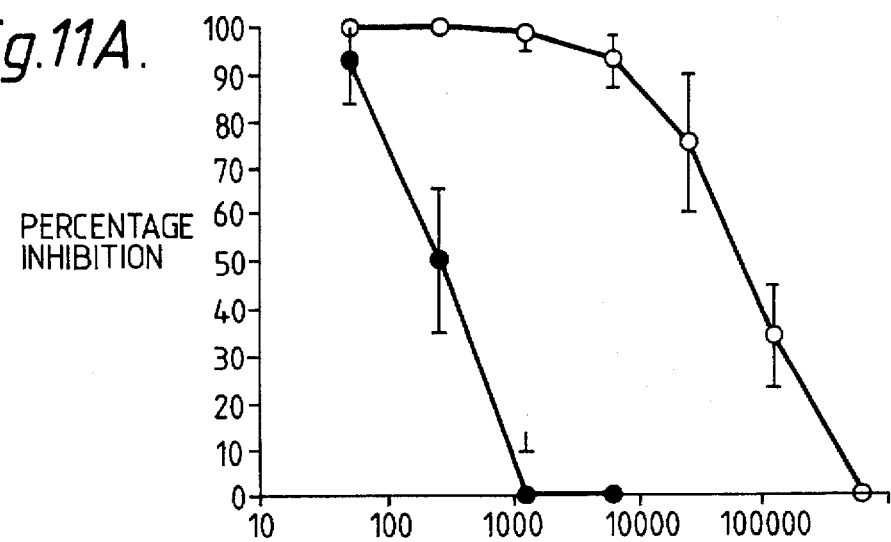
Figure 11B:
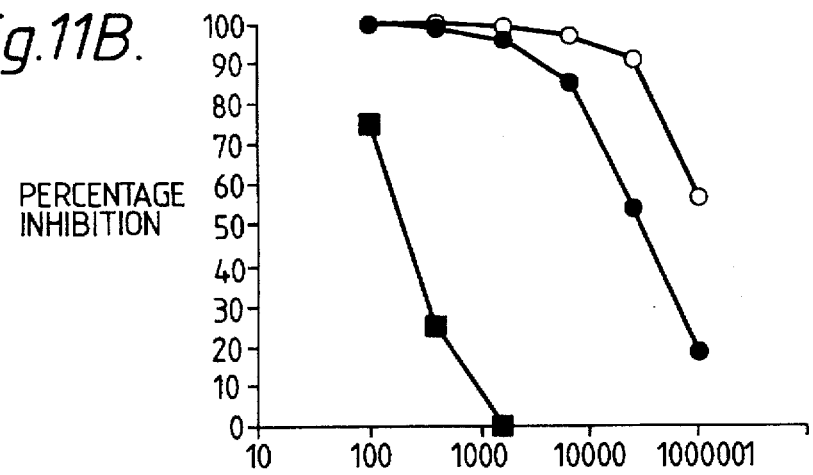
Figure 11C:
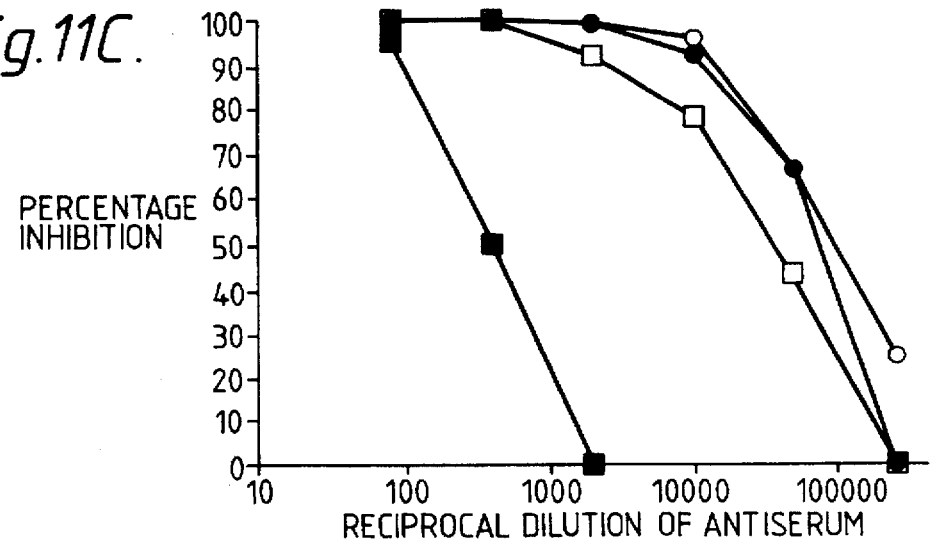

The finding that the inhibitory activity of antiserum against PI-KLH was partially removed by adsorption with liposomes containing PS suggested that inhibitory antibodies exist which bind to acidic phospholipids but not to the neutral phospholipid PC. We therefore examined the ability of antisera raised against PS-KLH to inhibit the induction of TNF by the toxic antigens. Again titres were greatly enhanced after 3 injections compared with those of antiserum obtained after one injection (FIG. 11a). This activity was remarkable, in that we had previously found that in contrast to PI, immunisation with unconjugated PS did not induce the production of inhibitory antiserum unless it was in liposomal form (16). Again most of the activity was in the IgG, rather than the IgM fraction (FIG. 11b). However, the antisera showed a different specificity from those against PI-KLH in that the inhibitory activity was largely removed by adsorption with PS, but was not significantly affected by PI, liposomes (11c). Pretreatment of macrophages with the antisera did not affect their subsequent ability to respond to the parasite antigens, including that inhibition was not due to any binding of antibody to receptors on the cells. We conclude that PS-KLH stimulates a different population of B cells from PI-KLH, hut both populations secrete antibodies which block the TNF-stimulating activity of the parasite antigens.

Prolongation of antibody production

Figure 12:
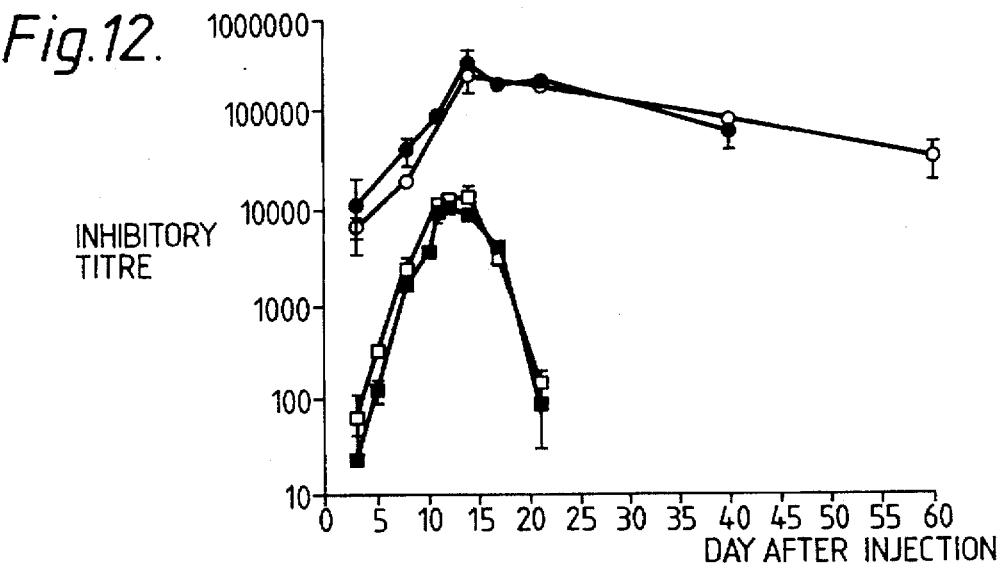

We had previously found that inhibitory antibody stimulated by one injection of *P. yoelii* toxic antigens was no longer detectable 30 days later (19). To see if its production was prolonged by immunization with a conjugated phospholipid, groups of mice were bold at intervals up to 2 months after the third injection of PI-KLH or PS-KLH and their sera assayed for inhibitory activity and compared with the results of titrations of antisera obtained after 3 injections of unconjugated PI or *P. falciparum* antigens (FIG. 12). Activity as great as the peak activity of serum from mice given the toxic antigens or unconjugated PI was present within 3 days. Furthermore its activity was strikingly prolonged and was still present 60 days later. At its peak the titre was more than 10 times higher.

Antisera against other phosphorylated compounds conjugated to KLH

Figure 13:
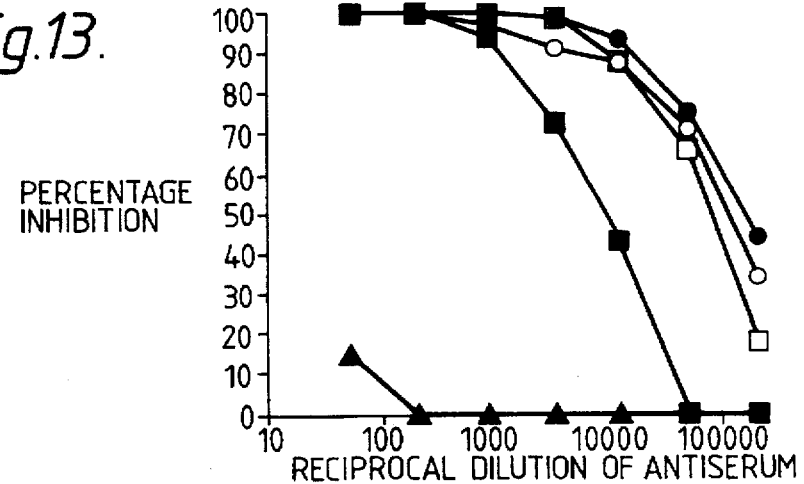
Figure 14A:
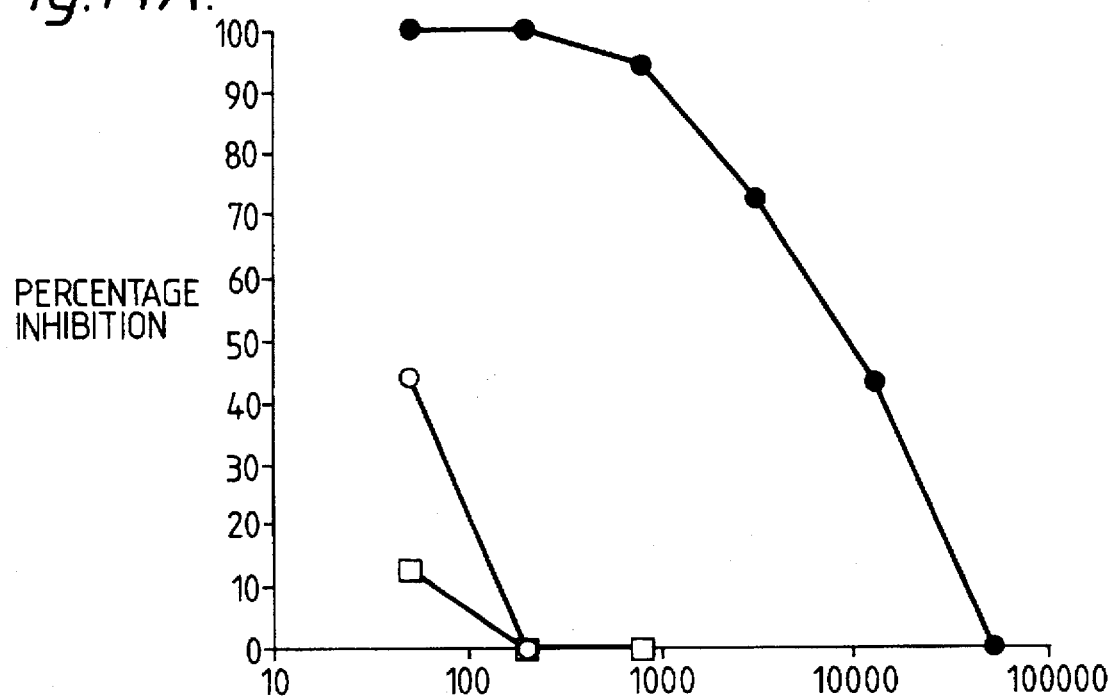
Figure 14B:
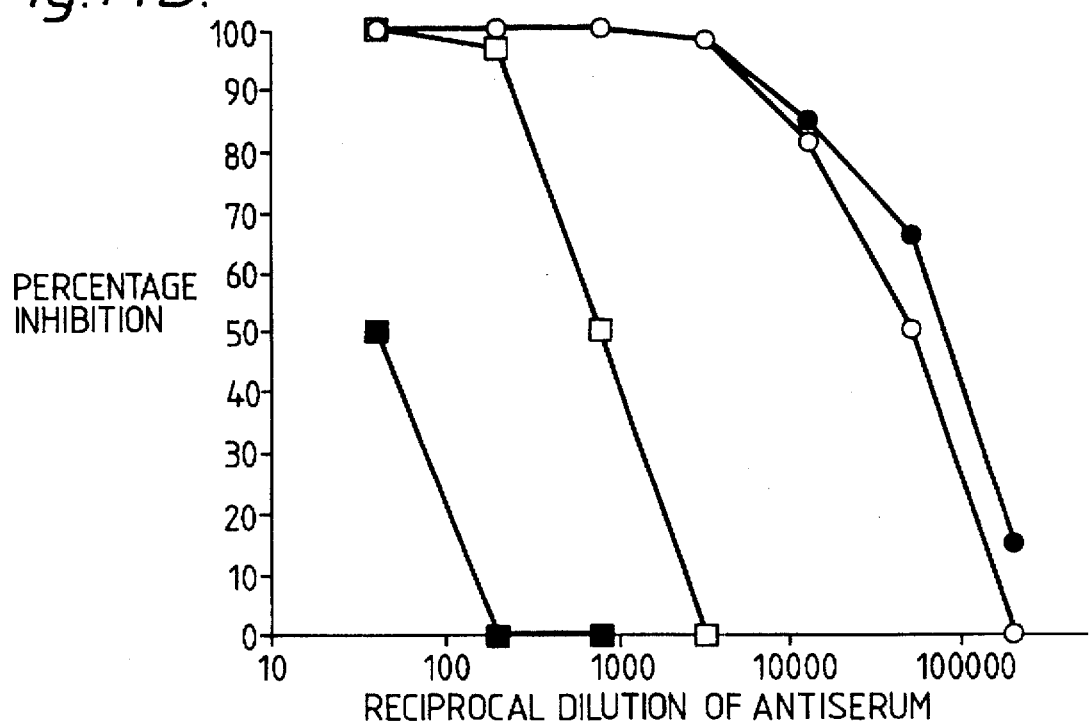

We previously found that a number of other phosphorylated compounds also stimulated the production of inhibitory antibody (unpublished work). To determine the effect of conjunction to KLH on their ability to induce the production of inhibitory antibody, mice were immunised with two of them selected for conjunction because they contained amino groups, namely phospho-threonine (P-Thr) and galactosamine-1-phosphate (Gal-1-P), and the inhibitory activity of their serum was compared with that of mice immunised with PI-KLH and PS-KLH (FIG. 13). No activity was detected in serum from a group of mice injected with lysine-KLH, indicating that the inhibitory antibody was induced by the phosphorylated molecules and not by the KLH carrier (or even by the EDC). The titres of Gal-1-P-KLH antisera were similar to those obtained with PI-KLH and PS-KLH, while those of P-Thr-KLH antisera were about 10-fold less. Again, titres were significantly higher after 3 injections than after 1 (data not shown). However the specificities of the antisera differed: thus the inhibitory activity of P-Thr-KLH antisera was removed by adsorption to PC or to PI liposomes (FIG. 14a), whereas PC liposomes had no effect on antisera against Gal-1-P-KLH, PI liposomes removed some of the activity, and PS liposomes removed most (FIG. 14b). It seems that antibodies against P-Thr-KLH bind to a comment epitope shared by many phospholipids, probably the phosphate ester head group. By contrast, the fact that inhibitory antibodies against Gal-1-P-

KLH were adsorbed by liposomes containing the two acidic phospholipids, PS and PI, suggests that charge might be a factor that affects their binding (23).

TNF secretion induced by other stimulants

Figure 15:
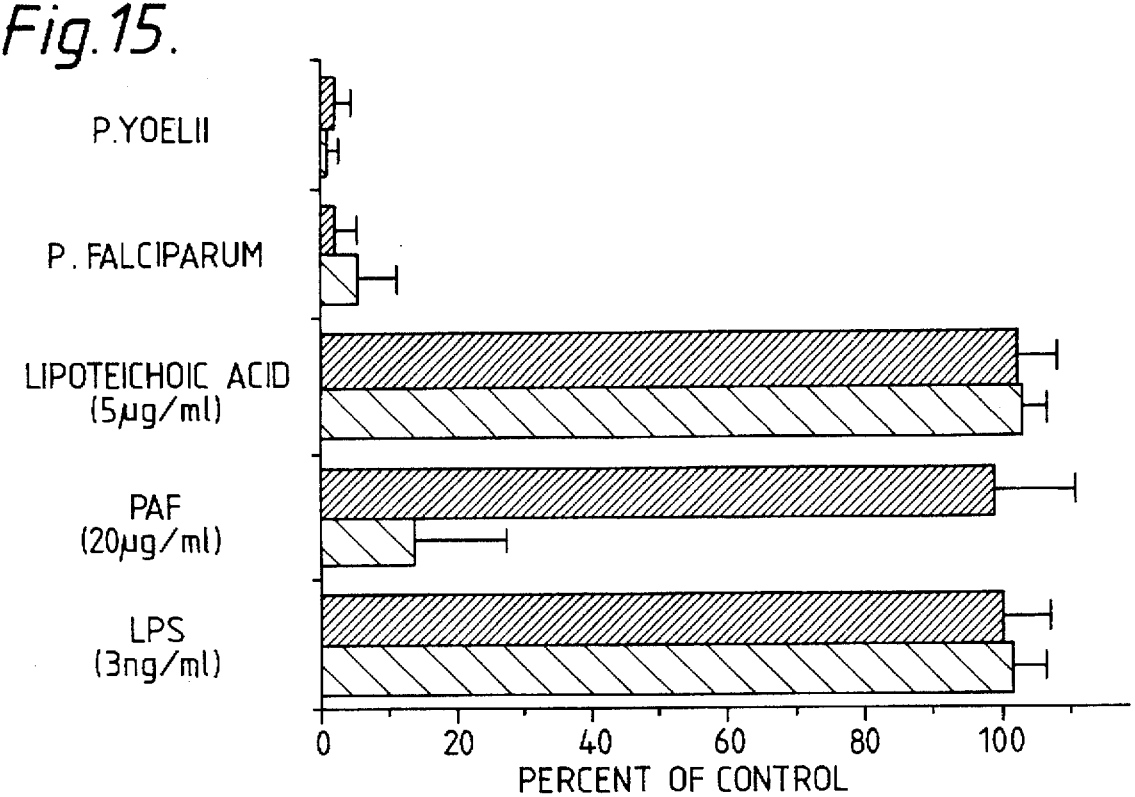

Since phospholipids are essential components of every cell membrane, it was possible that these antiphospholipid antibodies might bind to host cells. However the inhibitory activity of our antisera was not diminished by adsorption to normal mouse or human erythrocytes. Since antibodies against Plasmodium toxic antigens do not inhibit TNF induction by LPS (19), and antibodies against PI,IMP and various phospholipid liposomes which block TNF induction by the parasite antigens similarly are not active against LPS (16), we incubated PBMNC with some other stimulants known to induce the production of TNF, namely lipoteichoic acid (24) and platelet activating factor (PAF) (25), in the presence and absence of a 1/1500 dilution of antiserum against PI-KLH or PS-KLH (FIG. 15). At this dilution both antisera significantly reduced the amount of TNF produced in response to *P. yoelii* and *P. falciparum* antigens. They did not diminish the yield in response to LPS or lipoteichoic acid. However, while PI-KLH antiserum also did not affect the response to PAF, PS-KLH antiserum significantly inhibited the ability of this phospholipid to induce PBMNC to secrete TNF.

Induction of hypoglycaemia in immunized mice

Figure 16:
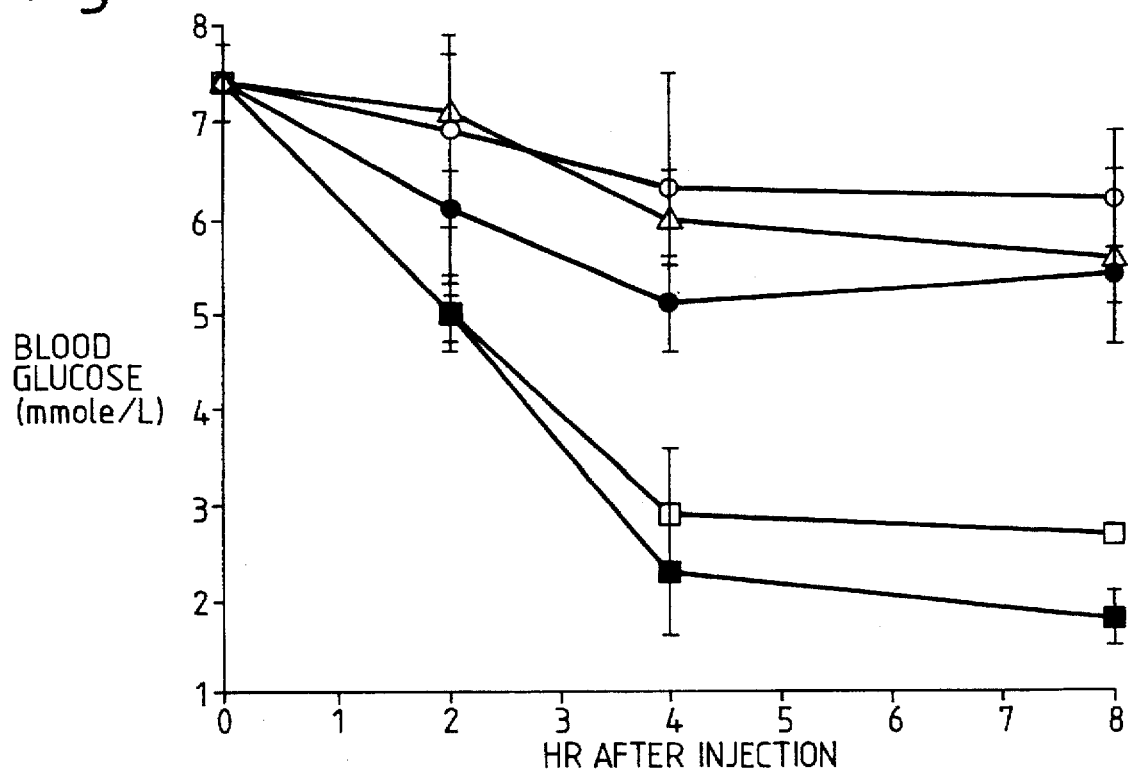
Figure 17:
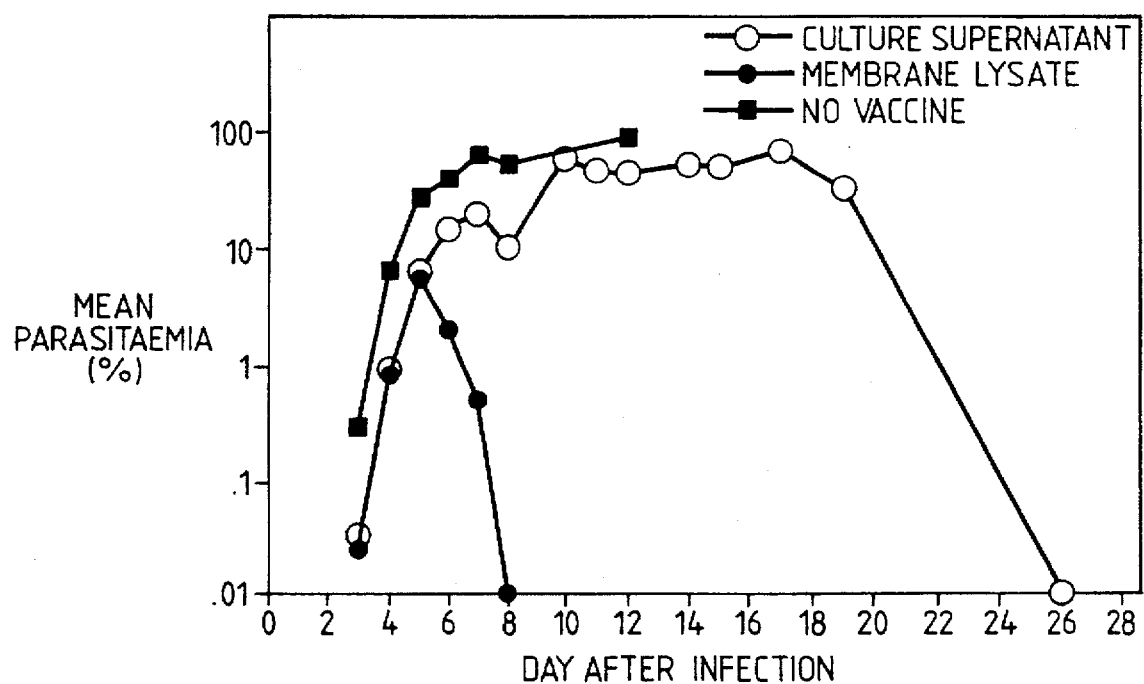
Figure 18:
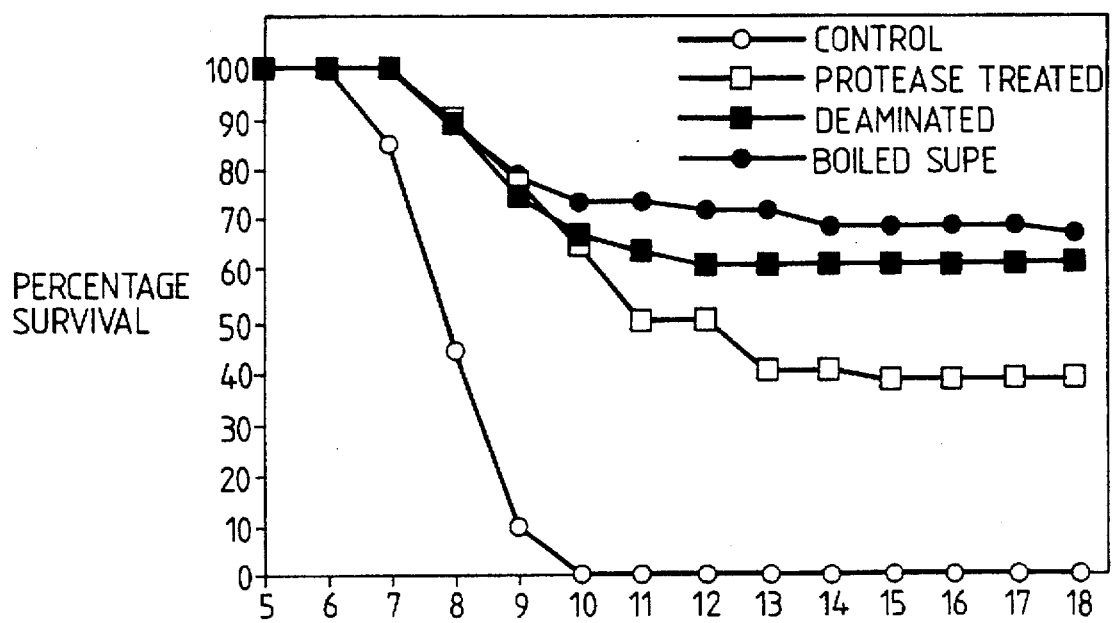
Figure 19:
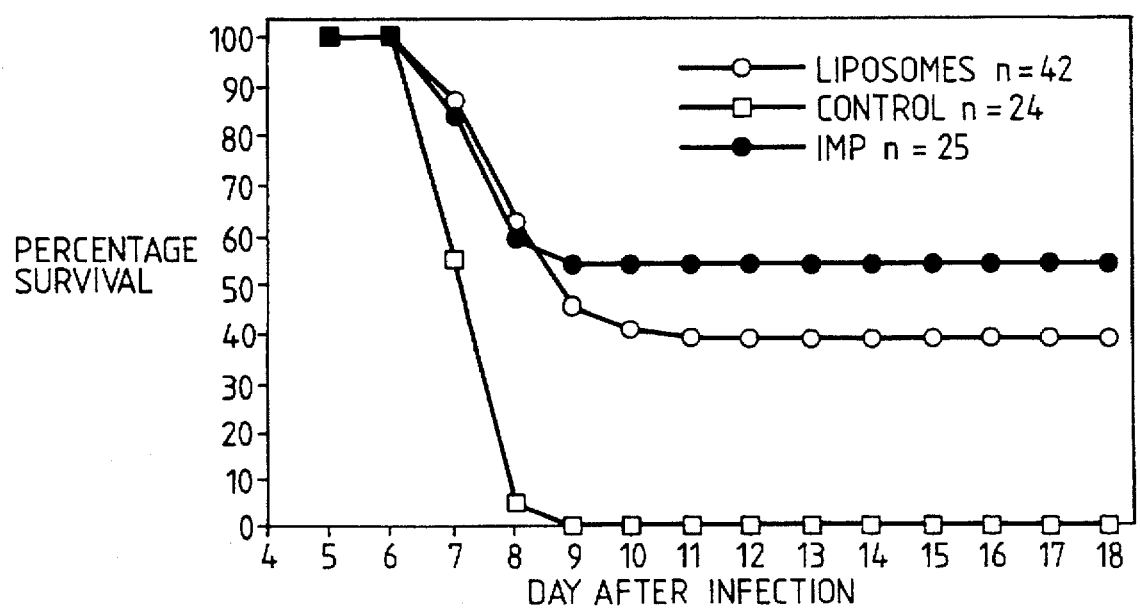

Mice immunized with *P. yoelii* toxic antigens do not show the same drop in blood glucose 4 hr after challenge with the toxic antigens as do control mice (22). We therefore challenged mice that had been immunized with some of the KLH conjugates similarly and measured their blood glucose at various times to see if they too were protected (FIG. 16). While the levels of unimmunized mice and of a group of mice that had been immunized with lysine-KLH were significantly lower at 2, 4 and 8 hr, those of mice immunized with PI-KLH did not drop below normal at any time; although those of mice immunized with PS-KLH and P-Thr-KLH showed a slight drop at 4 hr, they remained significantly higher than those of the control groups at all times.

Discussion

Three injections of the phosphorylated compounds PI, PS and Gal-1-P conjugated to KLH induced the production of high titres of antibodies that inhibited TNF induction by toxic malaria antigens. These appeared to be mainly IgG and more long lived than those made against the parasite phospholipid antigens, which were mainly IgM. The mean titre obtained after 3 injections of PI-KLH, for example, was 2–300,000 compared with the titres of 8–10,000 elicited by repeated injections of unconjugated PI or of the parasite antigens. There is evidence that the parasite antigens are normally associated with protein, in that their ability to induce the production of TNF is increased by treatment with a protease (14). Thus it might be expected that they would be capable of inducing a secondary IgG response without conjunction to a carrier, but we have found this not be be so (19).

The immunogens used were selected for a number of reasons: PI because it appears to form a critical part of the TNF-triggering parasite molecule (15,16); PS because it is also a negatively charged phospholipid; P-Thr because like PS and Gal-1-P it contains an amino group to which KLH could be coupled; Gal-1-P because it was one of a number of phosphorylated sugars, including mannose, glucose, galactose and fructose (but not glucosamine, oddly enough) which induced inhibitory antibody after 1 injection of 200 μg (unpublished work).

Of the four compounds, P-Thr-KLH gave rise to the lowest titres, although these were significantly higher than those obtained after injection of unconjugated P-Thr (unpublished work) and to the least specific antibodies. PS-KLH gave rise to the most specific, judging by the results of adsorption experiments with the different sorts of liposomes. As we argued previously, since PI inhibits TNF induction by the parasite antigens (15), and the inhibitory activity of antisera made both against the parasite antigens and against inositol monophosphate was removed specifically by PI liposomes (16), the active portion of the antigens seems likely to contain PI. However antibodies against PI-KLH were less specific than those obtained against unconjugated PI (16), since they also adsorbed to PS liposomes. This may arise because the binding of some inhibitory antibodies may be influenced by charge; liposomes incorporating PI and PS express a negatively charged surface, in contrast to those containing PC or cardiolipin, which are neutral (23). Although charge might also explain the specificity of the antisera against PS, it is possible that PS also forms part of the active moiety.

In the light of our previous findings (19,16), it was not surprising that these antisera did not inhibit TNF induction by LPS. Furthermore, they were also inactive against lipoteichoic acid, a component of the cell walls of Gram positive bacteria that contains poly(glycerophosphate) chains. Whereas in our experiments Lipoteichoic acid from *Staph. aureus* induced the secretion of TNF from human PBMNC, others have reported that it was inactive (24); however, the intraspecies variation they observed may account for our differences. PAF has been reported to stimulate human monocytes to secrete TNF in vitro (25). The PAF antagonist, 1-0-hexadecyl-2-acetyl-sn-glycero-3-phospho (N,N,N-trimethyl)hexanolamine, inhibits the induction of TNF by both LPS and by the toxic antigens of *P. yoelii*, implying that PAF might be generated as a second messenger in both cases (15). It was surprising that antiserum against PS-KLH but not against PI-KLH inhibited PAF-induced TNF secretion by PBMNC. As macrophages stimulated with cytokines are known to release PAF into the culture supernatant (26), it is possible that it reacted with extracellular PAF, however this explanation is unlikely since this antiserum did not also inhabit LPS-induced TNF secretion. Furthermore, although PAF is a modified PC, antibodies against PS-KLH were not removed by adsorption with PC liposomes. It is possible that different epitopes exist on PAF (27) which might not be expressed on PC liposomes or that inhibitory antibodies that might react with PC do not react with it in liposomal form.

Some anti-phospholipid antibodies cross-react with DNA (28) and the elicitation of such antibodies by parasite toxic antigens released during infection might explain why DNA-binding antibodies are found in the serum of patients with malaria (29). DNA-binding antibodies are also associated with autoimmune diseases such as systemic lupus erythematosis, raising the possibility that immunization with phospholipids might induce harmful autoimmune reactions. However, no pathological consequences have been reported in phase I and II trials of drug-containing liposomes (30) and experimental animals given repeated injections of phospholipids do not develop autoimmune disease. Furthermore, differences have recently been shown to exist between antiphospholipid antibodies associated with autoimmune disease and those associated with infection, including malaria (31).

We have observed that our toxic parasite antigens cause hypoglycaemia as well as induce TNF secretion. This does not appear to be due to the ability of TNF itself to induce hypoglycaemia (32) as pretreatment of mice with a monoclonal antibody against TNF did not prevent them from developing hypoglycaemia when challenged with the parasite toxic antigens (22). The finding that immunisation with PI, PS and P-Thr conjugated to KLH prevented the antigen-induced hypoglycaemia provides further support for our view that these hypoglycaemia-inducing molecules are also phospholipids. We suggested earlier that the toxic antigens of malaria, suitably detoxified and modified to induce IgG and memory, might form the basis of an anti-disease vaccine (17), which would protect individuals against the toxicity of malaria, whether mediated through the induction of cytokines or by other mechanisms. The results described here indicate one way in which such a goal might be achieved.

References

1. CERAMI A & BEUTLER B. (1988) The role of cachectin/TNF in endotoxic shock and cachexia Immunol. Today 9, 28.
2. CLARK I. A., CHAUDRHI G & COWDEN W. B. (1989) Roles of tumour necrosis factor in the illness and pathology of malaria. Trans. Roy. Soc. Trop. Med & Hyg. 83, 436.
3. KERN P., HEMMER C. J., VAN DAMME, J. GRUSS H-J & DIETRICH M. (1989) Elevated tumour necrosis factor a and interleukin-6 serum levels as markers for complicated Plasmodium falciparum malaria Amer. J. Med. 57, 139.
4. GRAU G. E., TAYLOR T. E., MOLYNEUX M. E., WIRIMA J. J., VASSALLI P., HOMMEL M. & LAMBERT P-H (1989) Tumour necrosis factor and disease severity in children with falciparum malaria N. Eng J. Med 320, 1586.
5. KWIATKOWSKI D., HILL A. V. S., SAMBOU I., TWUMASI P., CASTRACANE J., MANOGUE K. R., CERAMI A., BREWSTER D. R & GREENWOOD B. M. (1990) TNF concentration in fatal cerebral, non-fatal cerebral, and uncomplicated Plasmodium falciparum malaria. Lancet 336, 1201
6. POBER J. S., LAPIERRE L. A. STOLPEN A. H. BROCK T. A., SPRINGER T. A., FRIERS W., BEVILACQUA M. P., MENDRICK D. L. & GIMBRONE M. A. Jr. (1987) Activation of cultured human endothelial cells by recombinant lymphotoxin:comparison with tumour necrosis factor and interleukin 1 species. J Immunol 138, 3319.
7. BERENDT A. R., FERGUSON D. J. P. & NEWBOLD C. I. (1990) Sequestration in Plasmodium falciparum malaria: sticky cells and sticky problems. Parasitol. Today 6, 247.
8. KILBOURN R. G. & BELLONI F. (1990) Endothelial cell production of nitrogen oxides in response to interferon-g or combination with tumour necrosis factor, interleukin-1 or endotoxin. J. Natl. Cancer Inst. 82, 772.
9. CLARK I. A., ROCKETT K. A. & COWDEN W. B. (1991) Proposed link between cytokines, nitric oxide and human cerebral malaria. Parasitol Today, 7, 205.
10. BATE C. A. W., TAVERNE J. & PLAYFAIR J. H. L. (1988) Malarial parasites induce tumour necrosis factor production by macrophages Immunology, 64, 227.
11. TAVERNE J., BATE C. A. W. SARKAR D. A. MEAGER A., ROOK G. A. W. & PLAYFAIR J. H. L. (1990) Human and murine macrophages produce TNF in response to soluble antigens of Plasmodium falciparum. Parasite Immunol 12, 33.
12. PICOT S., PEYRON P., VUILLEZ J.-P., BARBE G., MARSH K. & AMBROISE-THOMAS P. (1990) Tumour necrosis factor production by human macrophages stimulated in vitro by Plasmodium falciparum. Infect. Immun., 58, 214.
13. BATE C. A. W., TAVERNE J. & PLAYFAIR J. H. L. (1989) Soluble malarial antigens are toxic and induce the production of tumour necrosis factor in vivo. Immunology, 66, 600.
14 BATE C. A. W. TAVERNE J ROMáN E., MORENO C. & PLAYFAIR J. H. L. (1992) TNF induction by malaria exoantigens depends upon phospholipid. Immunology. 75, 129.
15. BATE C. A. W., TAVERNE J. & PLAYFAIR J. H. L. (1992). Detoxified exoantigens and phosphatidylinositol derivatives inhibit TNF induction by malarial exoantigens. Infect. Immun. 60, 1984.
16. BATE C. A. W., TAVERNE J., BOOTSMA H. Z., MASON R. C. St-H., SKALKO N., GREGORIADIS G. & PLAYFAIR J. H. L. (1992) Antibodies against phosphatidylinositol and inositol monophosphate specifically inhibit TNF induction by malaria exoantigens. Immunology, 76, 35.
17. PLAYFAIR J. H. L., TAVERNE J., BATE C. A. W. & de SOUZA J. B. (1990) The malaria vaccine: anti-parasite or anti-disease? Immunol. Today, 11, 25.
18 BATE C. A. W., TAVERNE J., KARUNAWEERA N. D. MENDIS K. N. & PLAYFAIR J. H. L. (1992) Serological relationship of TNF-inducing exoantigens of P. falciparum and P. vivax. Infect. Immun 60, 1241.
19. BATE C. A. W., TAVERNE J., DAVÉ A. & PLAYFAIR J. H. L. (1990) Malaria exoantigens induce T-independent antibody that blocks their ability to induce TNF. Immunology 70, 315.
20. BUENAFE A. C & RITTENBERG M. B. (1991) Maturation of the antibody response to a protein coupled from the organophosphorous toxin soman. Immunology, 73, 398.
21. BREWSTER DR, KWIATKOWSKI D & N. J. (1990) Neurological sequelae of cerebral malaria in children. Lancet 336, 1039.
22. TAYLOR K., BATE C. A. W., CARR R., BUTCHER G., TAVERNE J. & PLAYFAIR J. H. L. (1992). Phospholipid-containing toxic antigens of malaria induce hypoglycaemia. Clin. exp. Immunol 90.1.
23. NISHIKAWA K., ARAI H. & INOUE K. (1990) Scavenger receptor-mediated uptake and metabolism of lipid vesicles containing acidic phospholipids by mouse peritoneal macrophages, J. Biol. Chem. 265, 5226.
24. BHAKDI S., KLONISCH T., NUBER P. & FISCHER W. (1991) Stimulation of monokine production by lipoteichoic acids, Infect. Immun 59, 4614.
25. VALONE, F. H. & RUIS N. M. (1992) Stimulation of tumour necrosis factor release by cytotoxic analogues of platelet activating factor. Immunology, 76, 24.
26. VALONE F. H. & EPSTEIN L. B. (1988) Biphasic platelet activating factor synthesis by human monocytes stimulated with IL 1b, tumour necrosis factor or IFN-g J. Immunol, 141, 3945.
27. SMALL M. A. BALDO B. A. & HARLE D. G. (1990) The specificity of the binding of platelet activating factor (PAF) to anti-PAF antibodies J. Mol. Recog. 3, 169.
28. STOLLAR B. D., McINERNEY T., GAVRON T., WASSEF N., SWARTZ GM. Jr & ALVING C. R. (1989) Cross-reactions of nucleic acids with monoclonal antibodies to phosphatidylinositol phosphate and cholesterol. Mol Immunol 26. 73.
29. WOZENCRAFT A. O. & STAINES N. A. (1990) DNA-binding antibodie and parasitic diseases. Parasitol. Today 6, 254.
30. GREGORIADIS G. (1990) Immunological adjuvants: a role for liposomes. Immunol. Today 11, 89.

31. HUNT J. E., McNEIL H. P., MORGAN G. J., CRAMERI R. M. & KRILIS S. A. A (1992) phospholipid-b-2-glycoprotein-1 complex is an antigen for anticardiolipin antibodies occurring in autoimmune disease but not with infection. Lupus 1, 75.

32. BAUSS F., DROGE, W., & MANNEL D. (1987). Tumour necrosis factor mediates endotoxic effects in mice. Infect. Immun., 55, 1622.

We claim:

1. A method of treating or preventing clinical manifestations of malaria, caused by infectious plasmodial organisms which express antigens which in the patient stimulate secretion of harmful levels of at least one cytokine, but which do not stimulate secretion of cytokines only by expression of lipopolysaccharide, which method comprises administering to a human in need thereof an effective non-toxic amount of an immunogen, wherein said immunogen is a pharmacologically acceptable material comprising inositol monophosphate or a phosphatidyl inositol, which immunogen stimulates production of antibodies which, in vitro, reduce or abolish secretion, by at least one of human monocytes and mouse peritoneal macrophages, of tumour necrosis factor following stimulation with a phospholipid-containing tumour necrosis factor-inducting antigen other than lipopolysaccharide.

2. A material for use in the treatment or prevention of clinical manifestations of malaria, caused by infectious plasmodial organisms which express antigens which in the patient stimulate secretion of harmful levels of at least one cytokine, but which do not stimulate secretion of cytokines only by expression of lipopolysaccharide, which material is an immunogen, wherein said immunogen is a pharmacologically acceptable material comprising inositol monophosphate or a phosphatidyl inositol, which immunogen stimulates production of antibodies which, in vitro reduce or abolish secretion, by at least one human monocytes and mouse peritoneal macrophages, of tumour necrosis factor following stimulation with a phospholipid-containing, tumour necrosis factor-inducing antigen other than lipopolysaccharide.

3. A method according to claim 1 wherein the immunogen also comprises a T-cell epitope.

4. A method according to claim 1 wherein the immunogen further comprises a carrier protein.

5. A material according to claim 2 wherein the immunogen further comprises a carrier protein.

6. The material according to claim 2, wherein the immunogen further comprises a T-cell epitope.

* * * * *